United States Patent
West et al.

(10) Patent No.: US 8,222,381 B2
(45) Date of Patent: *Jul. 17, 2012

(54) DERIVATIVES OF MONOSACCHARIDES FOR DRUG DISCOVERY

(75) Inventors: Michael West, Birkdale (AU); Peter Andrews, St. Lucia (AU); Tracie Elizabeth Ramsdale, Sunnybank Hills (AU); Wim Meutermans, Toowong (AU); Giang Thanh Le, Mt Gravatt (AU); Chris Clark, Taringa (AU); Giovanni Abbenante, Sampsonvale (AU); Ligong Liu, Sunnybank (AU)

(73) Assignee: Alchemia Limited, Queensland (AU)

( * ) Notice: Subject to any disclaimer, the term of this patent is extended or adjusted under 35 U.S.C. 154(b) by 53 days.

This patent is subject to a terminal disclaimer.

(21) Appl. No.: 10/524,048

(22) PCT Filed: Aug. 8, 2003

(86) PCT No.: PCT/AU03/01008
§ 371 (c)(1),
(2), (4) Date: Jun. 8, 2005

(87) PCT Pub. No.: WO2004/014929
PCT Pub. Date: Feb. 19, 2004

(65) Prior Publication Data
US 2006/0167237 A1   Jul. 27, 2006

(30) Foreign Application Priority Data
Aug. 8, 2002  (AU) .............................. 2002950657

(51) Int. Cl.
| C07H 15/04 | (2006.01) |
| C07H 15/10 | (2006.01) |
| C07H 15/14 | (2006.01) |
| C07H 15/20 | (2006.01) |
| C07H 5/06  | (2006.01) |
| C07H 17/00 | (2006.01) |

(52) U.S. Cl. .................... 536/17.5; 536/17.2; 536/17.6
(58) Field of Classification Search ............... 514/25
See application file for complete search history.

(56) References Cited

U.S. PATENT DOCUMENTS

| 4,376,207 A |   | 3/1983  | Uskokovic et al. |
| 4,495,346 A | * | 1/1985  | Anderson et al. ............ 536/18.5 |
| 4,548,923 A |   | 10/1985 | Hartmann et al. |
| 5,552,534 A |   | 9/1996  | Hirschmann et al. |
| 5,811,512 A |   | 9/1998  | Hirschmann et al. |
| 6,017,926 A |   | 1/2000  | Askew et al. |
| 6,030,942 A |   | 2/2000  | Cooperman et al. |
| 6,184,366 B1 |   | 2/2001  | Christ et al. |
| 6,417,172 B1 | * | 7/2002  | Rossignol et al. .............. 514/53 |
| 6,756,489 B1 |   | 6/2004  | Schmidt et al. |
| 7,138,531 B2 | * | 11/2006 | Sas et al. ...................... 549/267 |
| 7,232,900 B2 | * | 6/2007  | Johnson et al. ............... 536/120 |
| 7,417,129 B2 | * | 8/2008  | West et al. ...................... 536/4.1 |
| 7,994,140 B2 | * | 8/2011  | Meutermans et al. .......... 514/25 |
| 2003/0232766 A1 | * | 12/2003 | West et al. ...................... 514/42 |
| 2006/0223764 A1 |   | 10/2006 | Meutermans et al. |
| 2008/0176936 A1 | * | 7/2008 | Meutermans et al. ........ 514/460 |
| 2011/0165700 A1 | * | 7/2011 | Meutermans et al. ........ 436/501 |

FOREIGN PATENT DOCUMENTS

| DE | 102 59 844    | 7/2004  |
| WO | WO 93/17032   | 9/1993  |
| WO | WO 95/11686   | 5/1995  |
| WO | WO 97/28172   | 8/1997  |
| WO | WO 99/00406   | 1/1999  |
| WO | WO 99/07718   | 2/1999  |
| WO | WO00/42057  * | 7/2000  |
| WO | WO01/36433  * | 5/2001  |
| WO | WO 01/98270   | 12/2001 |
| WO | WO 02/32915   | 4/2002  |
| WO | WO02/085867 * | 11/2002 |
| WO | WO 03/082846  | 10/2003 |
| WO | WO 2004/014929| 2/2004  |
| WO | WO 2004/032940| 4/2004  |

OTHER PUBLICATIONS

Carey, F. and Sundberg, R. "Advanced Organic Chemistry, Part B:Reactions and Synthesis" Copyright 2001, Kulwer Academic/Plenum Publishers, pp. 831-835.*
Carey, F. and Sundberg, R. "Advanced Organic Chemistry, Part B:Reactions and Synthesis" Copyright 2001, Kulwer Academic/Plenum Publishers, pp. 822-830, herein referred to as "Carey et al. part B".*
Greene et al., "Protective Groups in Organis Synthesis, Third Edition" published 1999 by John Wiley and Sons, Inc, pp. 494-653.*
Greene et al., "Protective Groups in Organic Synthesis" published 1999 by John Wiley and Sons, Inc, pp. 494-653.*
Davies et al., "Semisynthetic Aminoglycoside Antibacterials. Part 8. Synthesis of Novel Pentopyranosyl and Pentofuranosyl Derivatives of Gentamine C1 and C1a" J. Chem. Soc. Perkin Trans. 1 (1981) pp. 2151-2167.*
Anderson et al., "The Aminolysis of Methyl 2 : S-Anhydro-D-ficranosides. Part II. Methyl 2:3-Anhydro-5-O-methyl-alpha-and-beta-D-lyxofuranosides" J. Chem. Soc. (1956) pp. 819-823.*
Kiso et al., "Synthesis of B-D-(1->6)-linked disaccharides of N-fatty acylated 2-amino-2-deoxy-D-glucose: an approach to the lipid A component of the bacterial lipopolysaccharide" Carbohydrate Research (1981) vol. 88 pp. C10-C13.*

(Continued)

Primary Examiner — Eric S Olson
(74) Attorney, Agent, or Firm — Nixon & Vanderhye P.C.

(57) ABSTRACT

New compounds and methods for the preparation of combinatorial libraries of potentially biologically active compounds are based on monosaccharides of formula I being a derivative of a furanose or pyranose form of a monosaccharide,

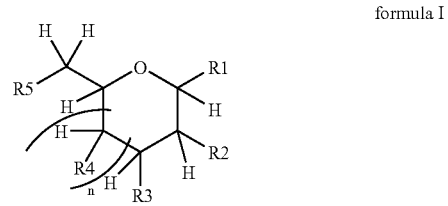

formula I 20 Claims, No Drawings

OTHER PUBLICATIONS

Fukase et al., "New Efficient Route for Synthesis of Lipid A by using Affinity Separation" Synlett (2001) No. 11 pp. 1693-1698.*

Danishefsky et al., "A Highly Convergent Total Synthetic Route to Glycopeptides Carrying a High-Mannose Core Pentasaccharide Domain N-linked to a Natural Peptide Motif" Chem. Eur. J. (1997) vol. 3 No. 10, pp. 1617-1628.*

Christ, W. J., "New monosaccharide derivatives, useful as intermediates for substituted liposaccharides for treating endotoxemia such as sepsis, septicemia and toxic shock", Derwent Abstract Accession No. 2002-371191/40, Mar. 7, 2002.

Maletic et al, "Preparation of Potential Inhibitors of the Mur-Pathway Enzymes on Solid Support Using an Acetal Linker", Bioorganic & Medicinal Chemistry Letters 13:1125-1128 (2003).

Fukase et al, "New Efficient Route for Synthesis of Lipid A by using Affinity Separation", Synlett 11:1693-1698 (2001).

Nakayama et al, "Novel peptidomimetics of the antifungal cyclic peptide Rhodopeptin: design of mimetics utilizing scaffolding methodology", Organic Letters 3(22):3447-3450 (2001).

Yoshizaki et al, "First total synthesis of the Re-type lipopolysaccharide", Angew. Chem., Int. Ed. 40(8):1475-1480 (2001).

Hanessian et al, "Formation of p-alkoxybenzylidene acetals on solid support and generation of functional diversity with carbohydrate scaffolds", Synlett 1:102-104 (1999).

Hirschmann et al, "Nonpeptidal Peptidomimetrics with a β-D-Glucose Scaffolding. A Partial Somatostatin Agoinst Bearing a Close Structural Relationship to a Potent, Selective Substance P Antagonist", J. Am. Chem. Soc. 114:9217-9218 (1992).

Gruner et al, "Carbohydrate-Based Mimetics in Drug Design: Sugar Amino Acids and Carbohydrate Scaffolds", Chem. Rev. 102:491-514 (2002).

Le et al, "Molecular diversity through sugar scaffolds", DDT 8(15):701-709 (2003).

Ye and Wong, "Anomeric Reactivity-Based One-Pot Oligosaccharide Synthesis: A Rapid Route to Oligosaccharide Libraries", J. Org. Chem. 65:2410-2431 (2000).

Office Action dated Jul. 8, 2010 issued in connection with U.S. Appl. No. 10/530,851.

International Search Report dated Jan. 15, 2004 issued in connection with PCT/AU2003/001347.

S. Budavari et al., "The Merck Index", Thirteenth Edition, pp. 793-794, monograph 4471.

Krocz et al, "G-Protein-Coupled Receptors [GPCRs] at a Glance", Journal of Cell Science 116:4867-4869 (2003).

Knapp et al, "Amino Alcohol and Amino Sugar Synthesis by Benzoylcarbamate Cyclization", J. Org. Chem. 55:5700-5710 (1990).

Ichikawa et al, "A new synthetic method for the preparation of amino sugars through an ally cyanate-to-isocyanate rearrangement", J. Chem. Soc. Perkin Trans. 1:1449-1455 (1997).

Bosserhoff, Anja-Katrin, "Integrins as targets in therapy", Expert Opin. Ther. Patents 16)7):963-975 (2006).

Arnaout et al, "Coming to grips with integrin binding to ligands: Opinion", Current Opinion in Cell Biology 14:641-651 (2002).

Boer et al, "Design, Synthesis, and Biological Evaluation of $\alpha_4\beta_1$ Integrin Antagonists Based on β-D-Mannose as Rigid Scaffold", Angew. Chem. Int. Ed. 40(20):3870-3873 (2001).

Clark and Brugge, "Integrins and Signal Transduction PathWays: The Road Taken", Science 268:233-238 (1995).

Hirschmann et al, "Modulation of Receptor and Receptor Subtype Affinities Using Diastereomeric and Enantiomeric Monosaccharide Scaffolds as a Means to Structural and Biological Diversity. A New Route to Ether Synthesis", Journal of Medicinal Chemistry 41(9):1382-1391 (1998).

Lehmann et al, "Role of αvβ5 and αvβ6 Integrin Glycosylation in the Adhesion of a Colonic Adenocarcinoma Cell Line (HT29-D4)", Journal of Cellular Biochemistry 61:266-277 (1996).

Longhi et al, "Involvement of Membrane Carbohydrates of HeLa Cells in the *E. coli* HB101 (pRI203) Invasive Pathway", Microbiologica 15:107-116 (1992).

Moitessier et al, "Design, Synthesis and Preliminary Biological Evaluation of a Focused Combinatorial Library of Stereodiverse Carbohydrate-Scaffold-Based Peptidomimetics", Bioorganic & Medicinal Chemistry 9:511-523 (2001).

Nicolaou et al, "Design, Synthesis and Biological Evaluation of Carbohydrate-Based Mimetics", Tetrahedron 53(26):8751-8778 (1997).

Stern et al, "Human Monocyte-Derived Macrophage Phagocytosis of Senescent Eosinophils Undergoing Apoptosis", American Journal of Pathology 149(3):911-921 (1996).

Du et al, "The recognition of three different epitopes for the H-type 2 human blood group determinant by lectins of Ulex europaeus, *Galactia tenuiflora* and *Psophocarpus tetragonolobus* (Winged Bean", Glycoconjugate Journal 11:443-461(1994).

* cited by examiner

US 8,222,381 B2

DERIVATIVES OF MONOSACCHARIDES FOR DRUG DISCOVERY

This application is the US national phase of international application PCT/AU2003/001008 filed on 8 Aug. 2003, which designated the US and claims priority to AU Application No. 2002950657 filed 8 Aug. 2002. The entire contents of these applications are incorporated herein by reference.

FIELD OF THE INVENTION

This invention relates to new compounds and methods for the preparation of combinatorial libraries of potentially biologically active compounds based on natural and unnatural monosaccharides.

These compounds are functionalized, with a view to varying lipid solubility, size, function and other properties, with the particular aim of discovering novel drug or drug-like compounds, or compounds with useful properties. The invention provides intermediates, processes and synthetic strategies for the solution or solid phase synthesis of monosaccharides, variously functionalised about the sugar ring, including the addition of aromaticity and charge, the addition of pharmacophoric groups and the placement of amino acid and peptide side chain units or isosteres thereof.

BACKGROUND OF THE INVENTION

In the field of drug discovery there is a constant need for novel scaffolds that enable the rational design of potentially bioactive molecules. Carbohydrates have recently come under scrutiny as offering a source of scaffolds that allow for a high degree of substitution, and offer access to both functional and structural diversity. The nature of monosaccharide molecules is such that there are numerous different stereoisomers available that can provide access to a greater degree of molecular space than do the scaffolds presently employed in drug discovery.

Carbohydrate monomers predominantly contain hydroxyl groups but also may contain other functionalities such as an amino and/or carboxylate function. In essence, the concepts involved in drug discovery through carbohydrate based molecular and structural diversity, are twofold: (1) The primary concept involves the exploitation of the high functional density found around the carbohydrate ring to display several different moieties of biological relevance. There is a dual significance to this substitution in that (i) the substituents relative position around the ring may be varied in relation to each other and, (ii) each individual moiety may be substituted for a class of such moieties and therefore themselves may be varied (by example: an arginine mimetic may be substituted at position 1, 2, 3, 4 or 5 around a ring in relation to other peptidomimetics, by the same token the arginine mimetic may represent a class of different arginine bioisosteres which may all be similarly substituted). (2) The second concept involves exploiting the structural diversity inherent in carbohydrate isomers. Each of the substituents around a carbohydrate ring may theoretically be presented in either an axial or equatorial configuration allowing access to hugely diverse molecular space. Many monosaccharides are naturally occurring, which aside from being useful in their own right, present themselves as cheap starting materials to access more exotic configurations.

There are other factors that promote carbohydrates as useful building blocks for drug discovery, for example the relative positions of the functional groups on the sugar rings are conveniently spaced such that they can effectively enable mimicry of (for example), peptide motifs such as peptidic turns and loops, as well as cyclic peptides.

The major difficulty encountered in attempts to employ monosaccharides as scaffolds, is associated with monosaccharide chemistry. In the past carbohydrate chemistry was considered arduous, protracted and not cost effective. Particularly, the degree of orthogonal protection group chemistry required to allow free access to any one of a monosaccharide's functional groups (usually five) was deemed too high to ever be effected in a commercially viable manner. As a corollary, the more easily effected peptide synthesis only requires a maximum three orthogonal protecting groups, additionally the conditions required for peptide synthesis are often milder, thus peptide synthesis has so far been able to be effected more easily than carbohydrate synthesis. Fortunately, recent developments in synthetic carbohydrate chemistry have begun to allow regular access to carbohydrates as molecular scaffolds. In a recent patent application (PCT AU00100025) we disclosed a range of orthogonally protected building blocks suitable for oligosaccharide synthesis. The building blocks presented in this application are also suitable for use as intermediates in the synthesis of compounds of the present invention, and represent compounds and methods which define the state of the art.

A large number of Carbohydrate based templates and scaffolds has now been published in the scientific literature. A review of the major contributions by Gruner et. al., (Chem. Rev., 2002, 102, p 491-514) highlights this activity. Within the general literature, there are two distinct types of carbohydrate templates (i) sugar amino acids and (ii) carbohydrate scaffolds.

Sugar amino acids are carbohydrates which contain both an amine function and a carboxylic acid function, and are used in place of amino acids in peptide type syntheses. The synthesis of monosaccharides for this purpose is exemplified by the work of Fleet (Tetrahedron, 1996, 52, p10711; Tetrahedron Assym., 1996, 7, p387; Tetrahedron Assym., 1996, 7, p157) and Le Merrer (Tet. Lett., 1995, 36, p6887) for furanoid sugars, and by Dondoni (J. Org. Chem., 1994, 59, p6404), Vogel (J. Carbohyd. Chem., 1994, 13, p37) and Kessler (see chem rev. above) for pyranoid sugars.

Sugar amino acids have been used in peptide synthesis, and in the formation of linear oligomers for various biological purposes (see chem reviews above). Importantly, all of these compounds contain an amino function and a carboxylate function directly attached to the carbohydrate ring, and these functional groups are involved in amide bond forming processes which is the central concept in their use. The compounds of this type are distinctly different from the compounds of the present invention.

Carbohydrate scaffolds have also received considerable attention in the scientific literature, at least by way of desideratum. In concept, these compounds provide a chiral scaffold on which pharmaceutically active moieties are presented. This is the field of the present invention which adds to and is distinct from the state of the art.

The use of carbohydrates as scaffolds was promulgated by Hirschmann and co workers (Hirschmann et. al., J. Am. Chem. Soc., 114, 9217-9218, 1992) who employed this concept to develop a potent NK-1 receptor antagonist (Hirschmann et. al., J. Am. Chem. Soc., 115, 12550-12568, 1993), (Hirschmann et. al., J. Med. Chem., 39, 2441-2448, 1996). The fundamentals of this work have also been patented by Hirschmann et. al. (PCT/US1994/012233).

In a similar manner, Papageorgiou et al, have applied the concept to furanoid structures, developing weak somatostatin inhibitors in the process (Papageorgiou et. al., Bioorg. Med. Chem. Lett., 2, 135-140, 1992).

Weak inhibitors of integrin receptors and endothelin receptors have also been developed by applying this concept (Nicolaou, K. C., et. al, Tetrahedron, 1997, 53, p8751; Moitessier, N., et. al., Lett. Pep. Sci., 1998, 5, p75; Moitessier, N., et. al., Bioorg. Med. Chem., 2001, 9, p511.).

A number of other research groups have developed libraries of compounds based on this scaffold principle, and these groups are referred to in Gruner's review (vide supra). Despite the plethora of work to date, the compounds disclosed above have three common features which distinguish them from the current work: (i) all of the substituents are attached to the scaffold through an oxygen linkage, (ii) the anomeric position is always an O glycoside, and (iii) all of the available hydroxyl positions are substituted.

These features, when taken together, place significant limitations on the utility of the compounds. For example, ether linkages provide considerable rotational freedom and it is generally accepted that rotational freedom often results in diminished biological activity (Murphy et. al., J. Org. Chem., 68, 5692-5704, 2003). To this end, the present invention is directed to carbohydrate templates which have one or two amines directly attached to the carbohydrate ring, allowing the introduction of, for example, amide linked, sulfonamide linked, urea linked and carbamoyl linked moieties with significantly reduced rotational freedom and often better physical properties.

In a similar manner, the requisite for all of the positions to be substituted can lead to compounds of higher lipophillicity, higher molecular weight and lower solubility without imparting greater biological activity. In the present invention we disclose compounds with one or two hydroxyl positions unsubstituted, allowing generally improved solubility characteristics and lower molecular weights that would be expected for the corresponding fully substituted molecules.

These two features represent significant improvements over compounds described in the literature and are the result of considerable new method developments by the inventors.

Of all the carbohydrate scaffold work reported in the scientific and patent literature to date, we have found few examples of amine containing scaffolds outside the sugar amino acid class. Kunz et. al. (WO 99/07718) have claimed 2-deoxy 2-amino sugars as scaffolds for drug discovery. This citation does not teach or exemplify a compound with an amine group directly attached to the ring in the two position or any other position.

The disclosures in Kunz's relate specifically to the use of glucose, galactose and mannose as scaffolds and the methods described are not generally applicable to other monosaccharide scaffolds. In contrast, the compounds of the present invention are all O glycosides which are further limited by a narrow range of unsubstituted substituents dictated by the low reactivity of the sugar hydroxyls under the synthetic conditions disclosed. It is apparent that this technology displays significant disadvantages to the present invention; the efficiencies of conversion, the range of potential substituents, the various inversion chemistries that introduce both alternate oxy and amino stereochemical orientations, and the versatile alkylative chemistries of the present invention represent significant improvements over the methods of Kunz's application. Particularly, the present invention provides stereoisomers of monosaccharides that have a nitrogen or a carbon atom attached to the ring in positions 3,4,5 and 6 of a monosaccharide or tetrahydrofurano/pyrano ring system. Of particular interest to the medicinal chemist is the inclusion of linking functionalities that are likely to be stable to physiological conditions thus allowing the drug to reach the desired target intact, or in an active form.

Despite the general paucity of amine containing carbohydrate scaffolds in the literature, there are many examples of monosaccharide building blocks and protected aminosugars employed for oligosaccharide synthesis. By way of example, U.S. Pat. No. 4,818,816 discloses a compound 1-methyl-2-carbobenzyloxy,3-benzyl glucosamine, a monosaccharide building block used in the synthesis of synthetic heparinoid oligomers. The compounds of the present invention represent a significant departure from the simple building block type aminosugars, both in the diversity and complexity which is achievable. In order, to further distinguish the compounds of the present invention from the prior art, the use of standard amine protecting groups in carbohydrate synthesis is specifically excluded.

Sabesan (U.S. Pat. No. 5,220,008) discloses a series of higher oligosaccharides as inhibitors on influenza. Within the claims of this patent, a partially protected monosaccharide (structure IV) is also disclosed. The compounds of this structure are protected monosaccharides for oligosaccharide synthesis which are known in the art and do not represent compounds for drug discovery.

Similarly, Alchemia Pty Ltd has disclosed in PCT/AU01/01307 building blocks, methods of syntheses, and final products relating to the employment of monosaccharide compounds as drug like molecules. The compounds of PCT/AU01/01307 are specifically directed at inhibitors of the muramyl cascade of enzymes and are hereby excluded from specification by the incorporation of this reference. A number of other publications relating to muramyl type compounds have appeared in the literature. Liu et. al. (Biorg. Med Chem Lett., 10, 2000, 1361-1363) present a series of compounds containing a benzyl glycoside at the anomeric position, an acetate at C-2 and a peptide homologated lactate at C-3 of a glucosamine scaffold. These compounds and those disclosed by Xiao (Peptides: Biol and Chem., Proc. 5th Int. Chinese Peptide Symp., 1998 CA: 134:178795) represent compounds and methods which help define the art of carbohydrate chemistry but are not directly relevant to the present invention.

It will be clearly understood that, if a prior art publication is referred to herein, this reference does not constitute an admission that the publication forms part of the common general knowledge in the art in Australia or in any other country.

OBJECT OF THE INVENTION

In a first aspect, the invention comprises a compound of formula I being a derivative of a furanose or pyranose form of a monosaccharide,

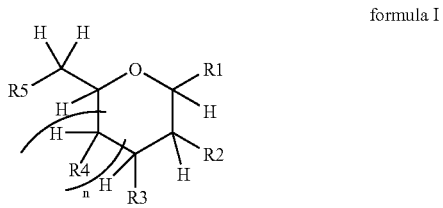

formula I

Wherein, n is 0 or 1;
R1 is XR wherein,
X is selected from O; S; S=O and SO$_2$,
R is selected from the group consisting of C1 to C9 alkyl, C1 to C15 alkenyl, C1 to C15 alkynyl, C1 to C15 heteroalkyl, C6 to C15 aryl, C6 to C15 heteroaryl, C6 to C15 arylalkyl or C6 to C15 heteroarylalkyl which is optionally substituted, cyclic or acyclic, branched and/or linear, The groups R2 to R5 are selected from OH, OR and N(Y)Z such that:

At least one of the groups R2 to R5 and not more than two of the groups R2 to R5 are OH, At least one of the groups R2 to R5 and not more than two of the groups R2 to R5 are OR, where R is defined above, with the proviso that when two of the groups R2 to R5 are OR, the R groups may not both be methyl or unsubstituted benzyl, At least one of the groups R2 to R5 and not more than two of the groups R2 to R5 are N(Y)Z, where Z is selected from hydrogen or R and Y is selected from the following, where G denotes the point of connection to the nitrogen atom in N(Y)Z, the N(Y)Z moieties may not be the same;

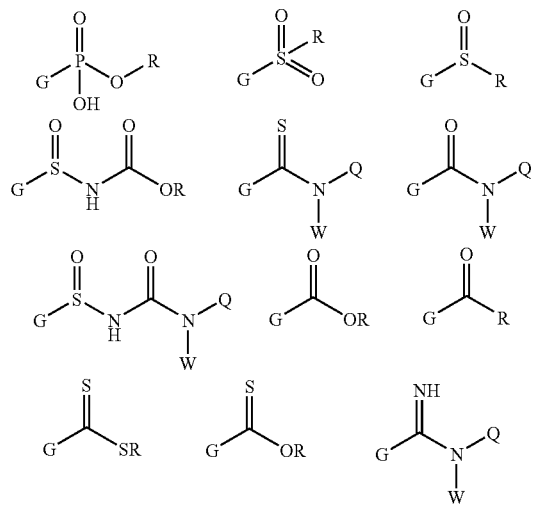

and the groups Q and W are independently selected from hydrogen or R as is defined above, and Q and W may combine to form a cycle, The groups Z and Y may combine to form a cycle, and The groups R1 to R5 may not combine together to form a cycle.

In a more particular form the invention resides in a compound as described above with the proviso that where two groups in the compound of formula I are N(Y)Z, these groups are different, with the further proviso that when either R2 or R5 is N(Y)Z, N(Y)Z may not be azido, acetyl, benzyloxycarbonyl or t-butoxycarbonyl, with the further proviso that when R2 is N(Y)Z, N(Y)Z may not be phthalimido, 4-[N-[1-(4,4-dimethyl-2,6-dioxocyclo-hexylidene)-3-methylbutyl]-amino}benzyl ester (ODmab), N-1-(4,4-dimethyl-2,6-dioxocyclohexylidene)ethyl (Dde), 2,2,2-Trichloroethoxycarbonyl (Troc), 9-Fluorenylmethoxycarbonyl (Fmoc), or a 5-Acyl-1,3dimethylbarbiturate type protecting group (DTPM) and with the further proviso that when the scaffold is of the 2-deoxy-2-aminoglucose configuration and R5 and R4 are both hydroxyl, R3 may not be a glycolate [—CH$_2$—CO$_2$H] or lactate ether [—CH(CH$_3$)—CO$_2$H] or an ester or amide derivative thereof.

Suitably, the compound is a derivative of a furanose form of a monosaccharide, and wherein n is 0.

Suitably, the compound is a derivative of a furanose form of a monosaccharide, and wherein n is 0.

Suitably, the compound has n=1, at least one of the groups R2 to R5 and not more than two of the groups R2 to R5 are N(Y)Z, where Z is selected from hydrogen or R and Y is selected from the following, where G denotes the point of connection to the nitrogen atom in N(Y)Z, the N(Y)Z moieties may not be the same;

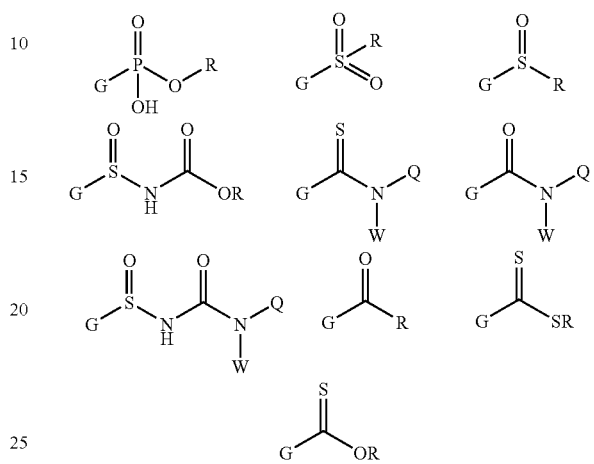

And the groups Q and W are independently selected from hydrogen or R as is defined above, with the proviso that Y and Z may not both be hydrogen and where two groups in the compound of formula I are N(Y)Z, these groups are different, the groups Z and Y may combine to form a cycle, the groups R1 to R5 may not combine together to form a cycle, with the proviso that where two groups in the compound of formula I are N(Y)Z, these groups are different, with the further proviso that when either R2 or R5 is N(Y)Z, N(Y)Z may not be azido, acetyl, benzyloxycarbonyl or t-butoxycarbonyl, with the further proviso that when R2 is N(Y)Z, N(Y)Z may not be phthalimido, 4[N-[1-(4,4-dimethyl-2,6-dioxocyclo-hexylidene)-3-methylbutyl]-amino}benzyl ester (ODmab), N-1-(4,4-dimethyl-2,6-dioxocyclohexylidene)ethyl (Dde), 2,2,2-Trichloroethoxycarbonyl (Troc), 9-Fluorenylmethoxycarbonyl (Fmoc), or a 5-Acyl-1,3-dimethylbarbiturate type protecting group (DTPM) with the further proviso that when the scaffold is of the 2deoxy-2-aminoglucose configuration and R5 and R4 are both hydroxyl, R3 may not be a glycolate [—CH$_2$—CO$_2$H] or lactate ether [—CH(CH$_3$)—CO$_2$H] or an ester or amide derivative thereof.

Suitably the heteroarylalkyl is substituted by a moiety from the group consisting of OH, NO, NO$_2$, NH$_2$, N$_3$, halogen, CF$_3$, CHF$_2$, CH$_2$F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, aminoaryl, aminoheteroaryl, thioalkyl, thioaryl or thioheteroaryl, which may be further substituted, with the proviso that the group R may not be or contain another saccharide moiety, a peptide, protein or amino acid.

The compound may be immobilized to a support. The support may be soluble or insoluble. Non-limiting examples of insoluble supports include derivatised polystyrene, tentagel, wang resin, MBHA resin, aminomethylpolystyrene, rink amide resin etc. Non-limiting examples of soluble supports include DOX-mpeg, polyethylene glycol etc.

DETAILED DESCRIPTION

Embodiments of the invention will be described with reference to the following examples. Where appropriate, the following abbreviations are used.

| | |
|---|---|
| Ac | Acetyl |
| DTPM | 5-Acyl-1,3-dimethylbarbiturate |
| Ph | Phenyl |
| TBDMS | t-Butyldimethylsilyl |
| TBDPS | t-Butyldiphenylsilyl |
| Bn | benzyl |
| Bz | benzoyl |
| Me | methyl |
| DCE | 1,2-dichloroethane |
| DCM | dichloromethane, methylene chloride |
| Tf | trifluoromethanesulfonyl |
| Ts | 4-methylphenylsulfonyl, p-toluenesulfonyl |
| DMF | N,N-dimethylformamide |
| DMAP | N,N-dimethylaminopyridine |
| α,α-DMT | α,α-dimethoxytoluene, benzaldehyde dimethyl acetal |
| DMSO | dimethylsulfoxide |
| DTT | dithiothreitol |
| DMTST | Dimethyl(methylthio)sulphoniumtrifluoromethanesulphonate |
| TBAF | tetra-n-butylammonium fluoride |

Part A: Preparation of Building Blocks:

In order to fully enable the invention, we detail below methods for the preparation of certain building blocks used in the preparation of the compounds of the invention. The building blocks described are suitable for both solution and solid phase synthesis of the compounds of the invention.

Example A

Synthesis of a 2,4 dinitrogen containing Galactopyranoside Building Block

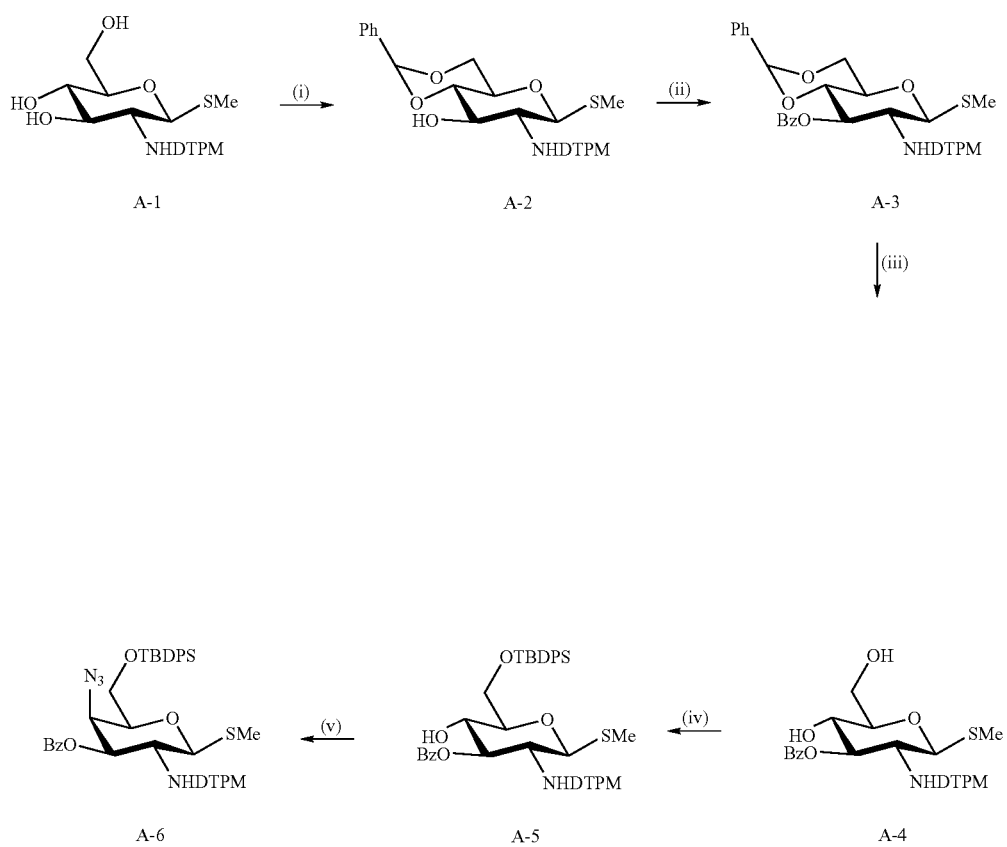

Conditions: (i) α,α-dimethoxytoluene (α,α-DMT), p-toluenesulphonic acid (TsOH), acetonitrile (MeCN), 76° C., 85%; (ii) Benzoylchloride (BzCl), triethylamine; DCM, 99%; (iii) methanol (MeOH)MeCN/water, TsOH, 75° C., 98%; (iv) t-butyldiphenylsilylchloride (TBDPS-Cl), imidazole, pyridine, 120° C., 99%; (v) Tf$_2$O, pyridine, DCM, 0° C., 100%; (b) NaN3, DMF, 16 hr, RT, 99%.

Example B

Synthesis of a 3-Nitrogen Containing Gulopyranoside Building Block

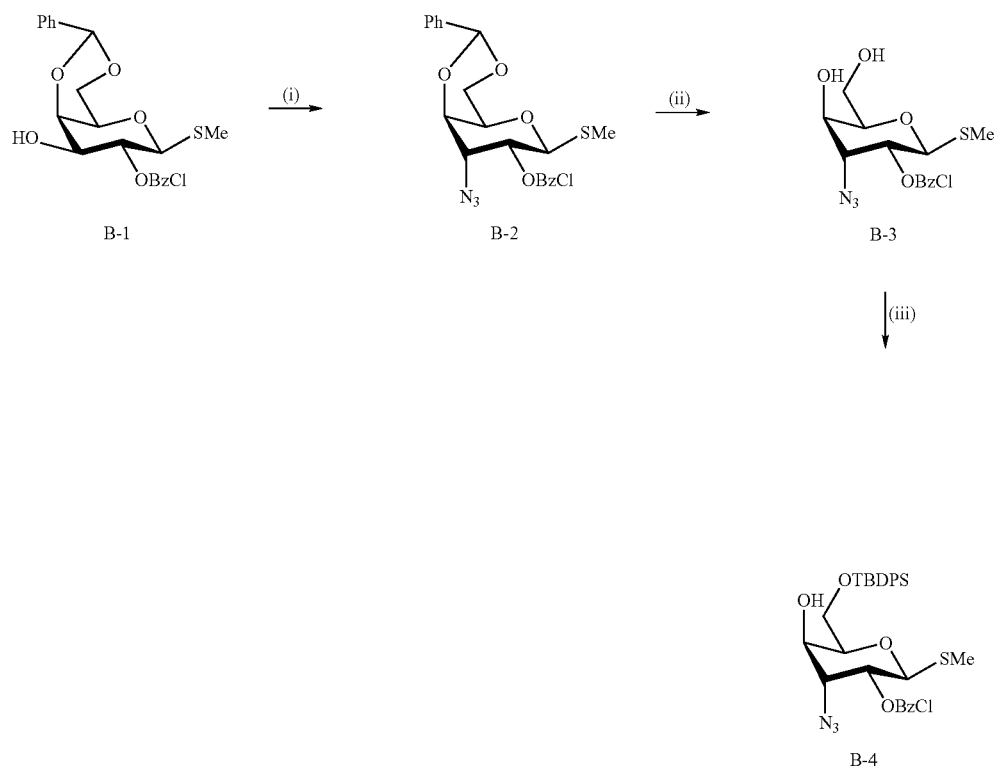

Conditions: (i) (a) trifluoromethanesulfonic anhydride (Tf$_2$O), pyridine, −20° C., dichloromethane (DCM), 1 hour, 100%, (b) sodium azide (NaN$_3$), N,N-dimethylformamide (DMF), 50° C., 5 hours, quantitative; (ii) TsOH, MeCN/MeOH/water (12:3:1), 90° C., 6 hours, 88% (iii) TBDPSCl, DMAP, pyridine, 120° C., 12 hours, 93%

Example C

Synthesis of a 2,6-Dinitrogen Substituted Glucopyranoside Building Block

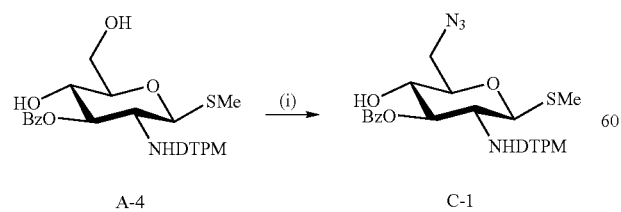

Conditions: (i) (a) Tosylchlodride, pyridine, RT, 24 hours, 33% (b) NaN$_3$, DMF, RT, 168 hours.

Example D
Synthesis of a 2-Nitrogen Containing Tallopyranoside Buildiong Block
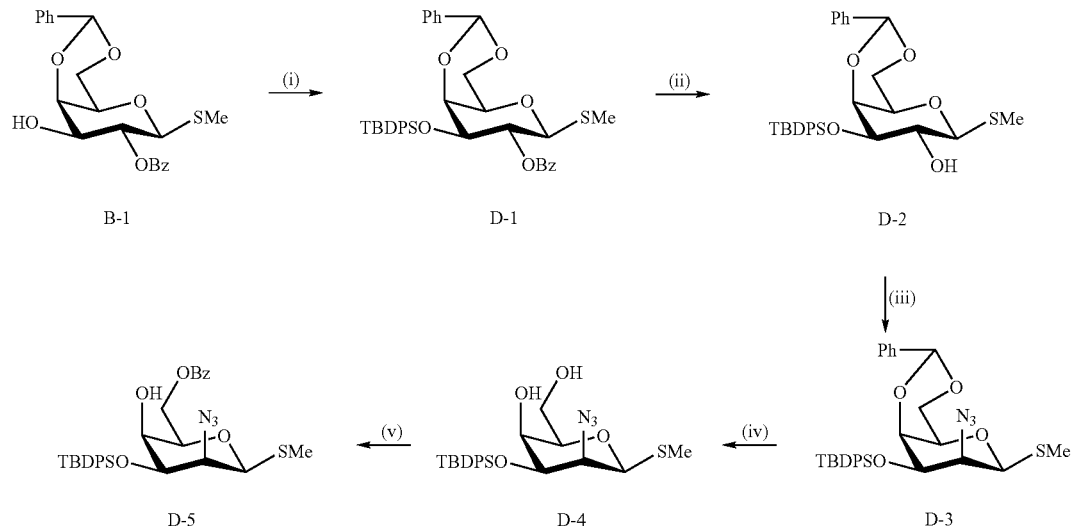
Conditions: (i) TBDPSCl, imidazole, 1,2-DCE, reflux; (ii) NaOMe/MeOH; (iii) (a) $Tf_2O$, pyridine, −20° C., DCM, 1 hour, (b) $NaN_3$, DMF, 50° C., 5 hours; (iv) TsOH, MeCN/MeOH/water; (v) benzoylchloride, DMAP, 1,2-DCE, −20° C.
Example E
Synthesis of Two 3-Nitrogen Containing Altropyranoside Building Block
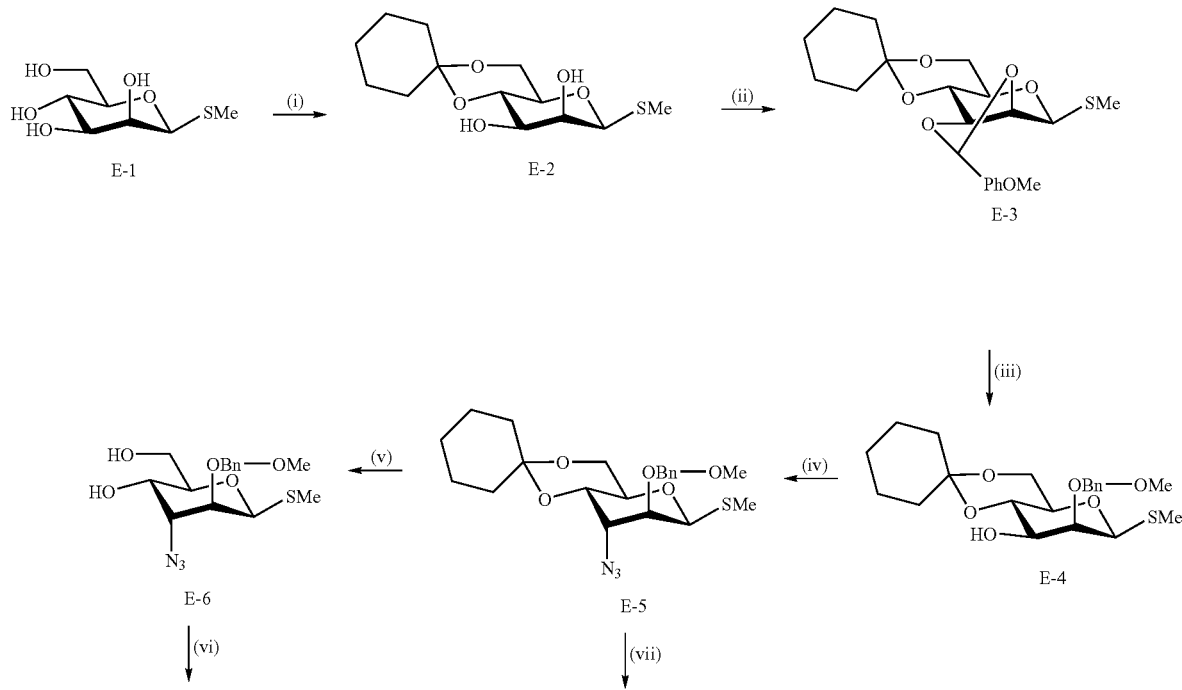

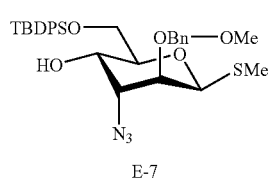
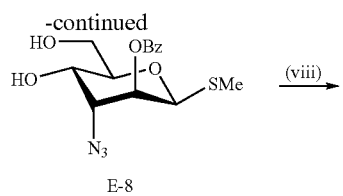
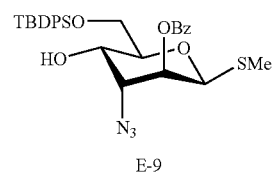

Conditions: (i) cyclohexanone dimethylacetal, TsOH, MeCN; (ii) p methoxybenzaldehyde dimethylacetal, TsOH, MeCN; (iii) DIBAL, −78° C., diethyl ether; (iv) (a) Tf$_2$O, pyridine, −20° C., DCM, 1 hour, (b) NaN$_3$, DMF, 50° C., 5 hours; (v) TsOH, MeCN/MeOH/water; (vi) TBDPSCl, DMAP, 1,2-DCE; (vii) (a) CAN, (b) BzCl, DMAP, 1,2-DCE, (c) TsOH, MeCN/MeOH/water, (viii) TBDPSCl, DMAP, 1,2-DCE.

Example F

Synthesis of a 2-Nitrogen Containing Glucopyranoside Building

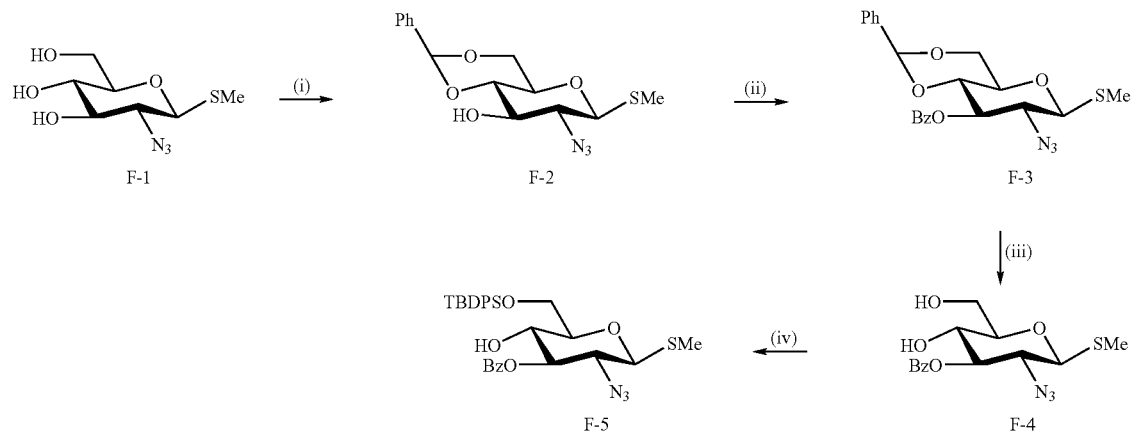

Conditions: (i) α,α-DMT, TsOH, MeCM; (ii) 1,2-DCE, BzCl, DMAP; (iii) TsOH, MeOH/MeCN; (iv) TBDPS-Cl, DMAP, 1,2-DCE.

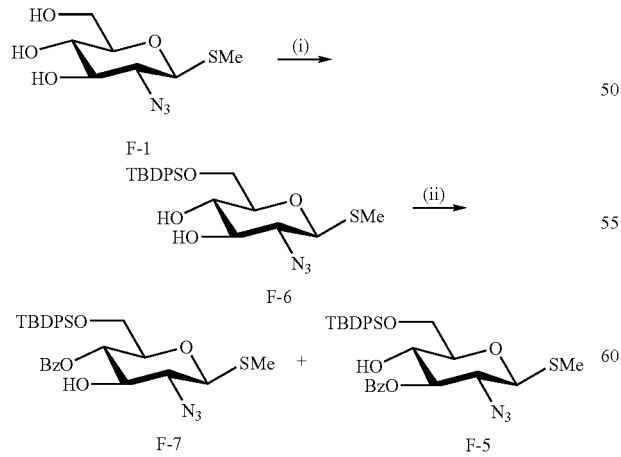

Conditions: (i) TBDPSCl, DMAP, pyridine, 120° C., 0.5 hours, 81%; (ii) a. (Bu)2SnO, MeOH; b. Benzoylchloride, RT, 24 hour;

Example G
Synthesis of a 2-Nitrogen Containing Allopyranoside Building Block
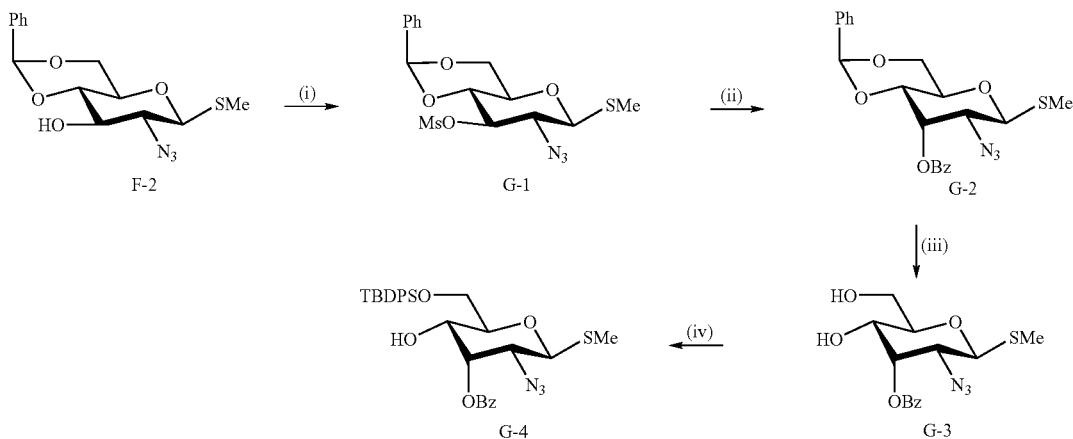
Conditions: (i) DCM/pyridine, MsCl, DMAP, 0° C.; (ii) sodium benzoate, dimethylsulphoxide (DMSO), 140° C.; (iii) TsOH, MeOH/MeCN/water; (iv) TBDPS-Cl, imidazole, DCM, 1 hour, reflux.
Example H
Synthesis of a 3Nitrogen Containing Allopyranoside Building Block
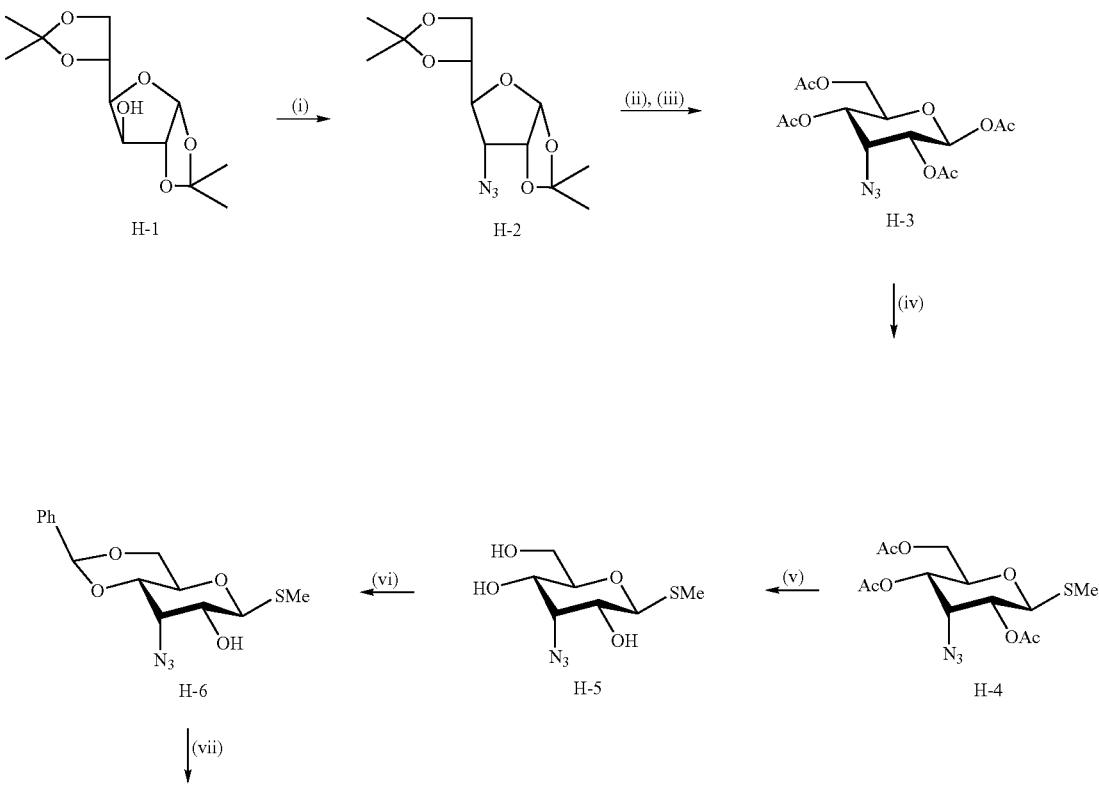

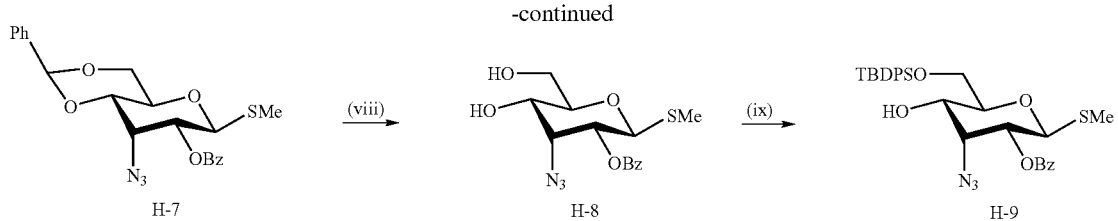

Conditions: (i) Tf$_2$O, pyridine, DCM; (b) NaN$_3$, DMF; (ii) acetone, H$^+$; (iii) Ac$_2$O, pyridine; (iv) hexamethyldisilazane, I$_2$, CH$_3$—S—S—CH$_3$; (v) NaOMe/MeOH; (vi) TsOH, ☐,☐-dimethoxytoluene, MeCN; (vii) benzoylchloride, 1,2-DCE, pyridine, DMAP; (viii) TsOH, MeOH, H$_2$O, MeCN; (ix) TBDPS-Cl, imidazole, 1,2-DCE.

Example I

Syntheses of Two 2-Nitrogen Containing Tallopyranoside Building Blocks with Hydroxyls in the 3 or 4 Positions

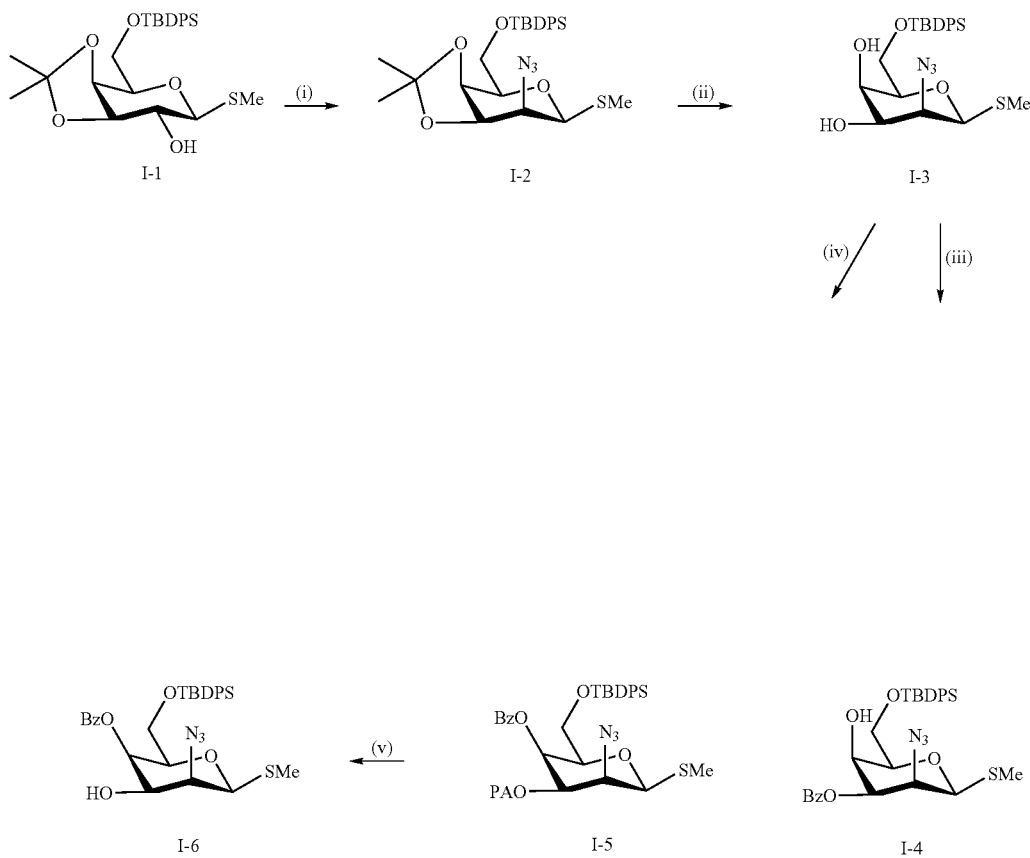

Conditions: (i) (a) Tf$_2$O/Py, (b) NaN$_3$, DMF; (ii) TsOH, MeOH/MeCN/water; (iii) BzCl, DMAP, 1,2-DCE; (iv) (a) phenoxyacetyl-Cl (PACl)/pyridine; (b) Bz$_2$O/pyridine; (v) MeNH$_2$/THF.

Example J
Synthesis of Nitrogen Containing Furanoside Building Blocks
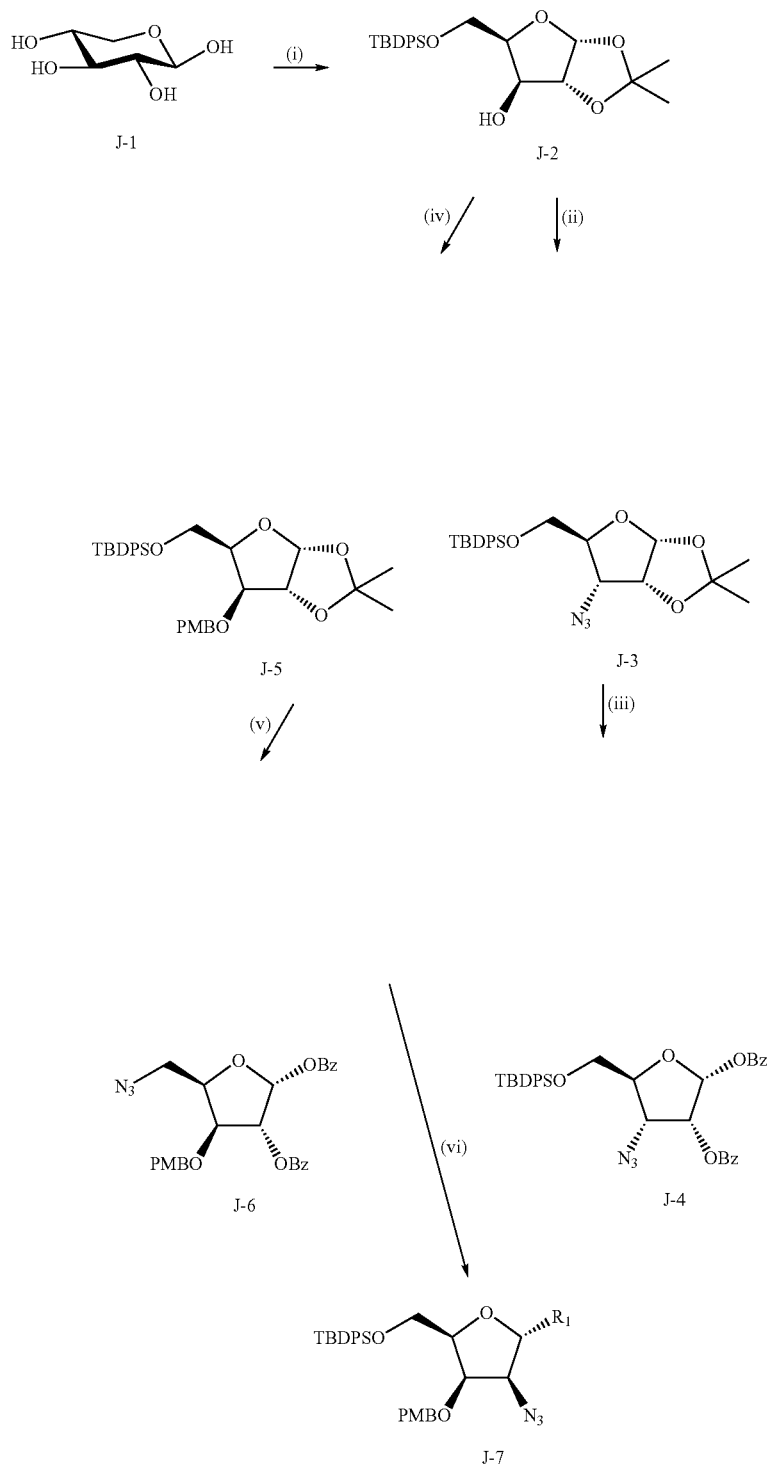
Conditions: (i) (a). 2,2-dimethoxypropane, TsOH, DMF; (b). TBDPSi-Cl, Imidazole, DMF; (ii) (a) Tf$_2$O/Py, (b) NaN$_3$, DMF; (iii) (a) TsOH, MeOH/MeCN/water; (b) Benzoyl chloride, pyridine, DCM; (iv) 4-methoxybenzyl chloride, NaH, DMF; (v) (a)TBAF, THF; (b) Tf$_2$O/Py, (c) NaN$_3$, DMF; (d) TsOH, MeOH/MeCN/water; (e) Benzoyl chloride, pyridine, DCM; (vi) (a) TsOH, MeOH/MeCN/water; (b) Benzoyl chloride, pyridine, DCM; (c) R—OH or R—SH, boron trifluoride diethyl etherate, DCM, molecular sieves; (d) Tf₂O/Py, (e) NaN₃, DMF;

Example K

Synthesis of a 3-Nitrogen Containing Gulopyranoside Building Block

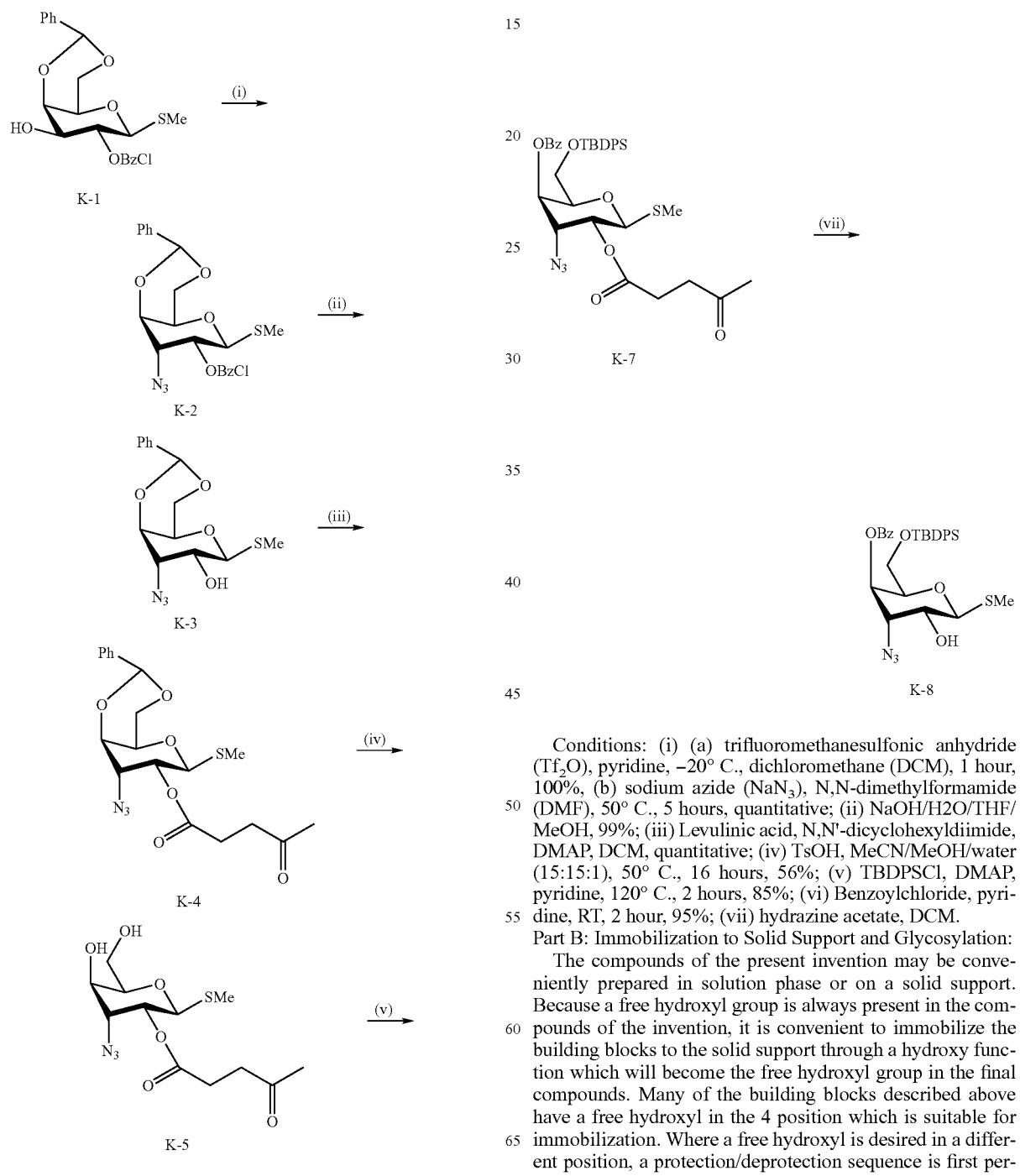

Conditions: (i) (a) trifluoromethanesulfonic anhydride (Tf₂O), pyridine, −20° C., dichloromethane (DCM), 1 hour, 100%, (b) sodium azide (NaN₃), N,N-dimethylformamide (DMF), 50° C., 5 hours, quantitative; (ii) NaOH/H2O/THF/MeOH, 99%; (iii) Levulinic acid, N,N'-dicyclohexyldiimide, DMAP, DCM, quantitative; (iv) TsOH, MeCN/MeOH/water (15:15:1), 50° C., 16 hours, 56%; (v) TBDPSCl, DMAP, pyridine, 120° C., 2 hours, 85%; (vi) Benzoylchloride, pyridine, RT, 2 hour, 95%; (vii) hydrazine acetate, DCM.

Part B: Immobilization to Solid Support and Glycosylation:

The compounds of the present invention may be conveniently prepared in solution phase or on a solid support. Because a free hydroxyl group is always present in the compounds of the invention, it is convenient to immobilize the building blocks to the solid support through a hydroxy function which will become the free hydroxyl group in the final compounds. Many of the building blocks described above have a free hydroxyl in the 4 position which is suitable for immobilization. Where a free hydroxyl is desired in a different position, a protection/deprotection sequence is first performed.

Example L

Alternative Immobilization Positions

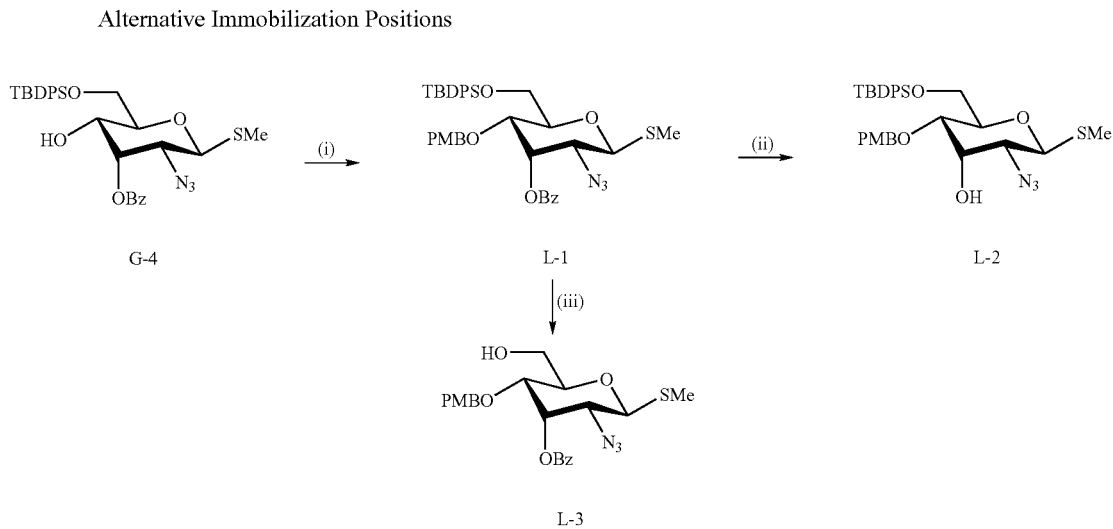

Conditions: (i) 4-methoxybenzyl chloride, NaH, DMF, workup with citric acid (ii) NaOMe/MeOH/THF; (iii) TBAF/THF; HOAc to neutral pH

Example M

Glycosylation of Anomeric Position

In most cases the thiomethyl glycoside building block containing one free hydroxyl group can be used in glycosylation reactions without resorting to protection of the free hydroxyl. An excess of the alcohol acceptor is typically employed. Where a thiol is to be glycosylated, the acceptor alcohol is in short supply or results are not satisfactory, the thiomethyl glycoside donor may first be converted to the bromo sugar or imidate, and these donors used for glycosylation. Alternatively, glycosylation can be effected with the fully protected precursor e.g. K-2, if significant side reaction is observed with the free hydroxy donors e.g. K-3, K-4, G-4.

In a typical proceedure, 1 mmol of donor (eg G-4, K-2, K-3, K-4, A-6, B-4, C-1 etc) is dissolved in anhydrous dichloromethane 8 mL and an equal weight of dry 4A molecular sieves is added. The mixture is stirred for 30 minutes at room temperature then 4 mmol of the acceptor alcohol is added followed by addition of DMTST solution (6 equivalents in 12 ml of DCM). The reaction is monitored by t.l.c. When the reaction is complete, triethylamine (1.2 mmol) is added. The mixture is diluted with 100 mL dichloromethane and extracted with sodium bicarbonate (10% aqueous), citric acid (10% aqueous) and sodium chloride (sat. solution), dried over magnesium sulfate and solvents removed in vacuo. The crude material is chromatographed on silica gel prior to immobilisation or in the case of K-2 removal of one of the alcohol protecting groups.

In an alternative proceedure, 1 mmol of donor in dichloromethane 8 mL is first treated with bromine to yield the crude sugar halide. This solution is washed breifly with 5% sodium thiosulfate, dried over magnesium sulfate and the solvents removed in vacuo. The crude sugar halide is used directly as above with silver triflate as the activating agent in place of DMTST. Both alcohols and thiols are amenable to glycosylation by this method.

Example N

Immobilization Onto Solid Phase

Wang resin (13.3 g; 0.85 mmol/g, p-Benzyloxybenzyl Alcohol polystyrene-divinylbenzene resin) was dried in the vacuum oven overnight in 500 ml round bottom flask. The flask was place under nitrogen atmosphere then dry DCM (133 ml) and trichloroacetonitrile (20 ml) was added. The mixture was cooled with ice bath while gently stirred. After 15 minutes of cooling DBU (1.3 ml) was added drop wise in 15 minutes, the resulting mixture was stirred for one hour with ice bath cooling. The resin was collected by filtering, washed with DMF, THF and DCM (3× each). The resin was dried in the vacuum oven over $P_2O_5$ for 24 hours to afford 15 grams of TriChloroAcetimidate Wang (TCA-Wang) resin. The resin was packed under nitrogen and stored at 4° C.
Yield 100%; loading ca. 0.754 mmol/g.
(Alternative Resins May be Used).

Glycosylated building blocks containing one free hydroxyl are immobilised onto TCA-Wang resin. In a typical proceedure, TCA Wang resin (3.6 gram) was dried in vacuum oven overnight then washed with anhydrous THF (3×36 ml) under nitrogen atmosphere. Building block (3 equiv.) was added followed by addition of anhydrous DCM (18 ml). The reaction mixture was shaken for 5 minutes (until all alcohol was dissolved), and $BF_3.Et_2O$ (0.35 ml, 1 equvalent) was added. The reaction mixture was shaken vigorously for ten minutes and drained; the resin was washed with DCM (3×30 ml), DMF (3×30 ml), THF (3×30 ml) and dried.

Part C: Library Preparation:

The compounds of the invention are prepared by sequential deprotection and ligation chemistries either on solid support or in solution phase. The following typical chemistries may be employed as required.

Removal of a Tert-Butyldiphenylsilyl:

The resin bound building block is suspended in dry THF/methanol (20/1 v/v) mixture containing 10 equivalents of tetra-n-butylammonium fluoride. The mixture is stirred at 65° C. for 24 hours, drained; the resin is filtered, washed with dimethylformamide followed by THF and finally dichloromethane. In an alternative procedure, TBAF may be conveniently replaced by HF.pyridine and the reaction effected in plastic ware. The TBAF may also be replaced by HF."proton sponge" complex with good results.

Removal of a Benzoate, p-Chlorobenzoate or Other Ester Protecting Group:

The resin bound building block is suspended in dry THF and methanol (3/1 v/v) mixture and sodium methoxide (0.5 equivalents) is added. The mixture is shaken for 24 hours, drained and re-treated with fresh reagents for further 24 hours. The resin is filtered, washed with dimethylformamide followed by THF and finally dichloromethane.

Removal of a p-Methoxybenzyl Group:

The resin bound building block is suspended in DCM and a small amount of water is added (approx 1%) followed by 2,3-dichloro-5,6-dicyanobenzoquinone (10 equivalents). The mixture is shaken for 3 hours drained and re-treated with fresh reagent for a further 3 hours. The resin is filtered, washed with THF followed by methanol and finally dichloromethane.

Etherification of Hydroxyl Position:

Resin bound building block which has previously had a hydroxyl group deprotected is washed three times and then suspended in anhydrous DMF and 3 equivalents of potassium t-butoxide added (alternative bases may be employed), shaken and drained after 5 minutes followed by the alkylating agent (3 equivalents) in DMF. The mixture is shaken for 10 minutes, drained and re-treated twice more with fresh reagents as above. The resin is filtered, washed with dimethylformamide followed by THF and finally dichloromethane.

Reduction of an Azide:

The resin bound building block is suspended in dry DMF; 5 equivalents of DTT (1,4-dithio-DL-threitol) and 3 equivalents of potassium tert-butoxide (alternative bases may be employed) are added. The mixture is agitated under nitrogen atmosphere for 24 hours, drained and the resin is washed with dimethylformamide followed by THF and finally dichloromethane.

Removal of a DTPM Group:

The resin bound building block is suspended in DMF and hydrazine hydrate (50/1 v/v) mixture, agitated 2 hours, drained and the resin is washed with dimethylformamide followed by THF and finally dichloromethane Amide Formation:

A solution of a suitable carboxylic acid (10 equivalents) in dry DMF is treated with HBTU (10 equivalents) and di-isopropylethylamine (10 equivalents) and shaken for 5 minutes. This solution is then added to a suspension of Resin bound building block, which has previously had an amine group deprotected in DMF and the mixture shaken for 30 minutes. After this time the resin is drained and treated once more with fresh reagent for 30 minutes. The resin is filtered, washed with DMF followed by methanol and finally dichloromethane. If desired, quantitative ninhydrin assay may be performed to determine that the reaction is complete. Alternative coupling systems including HOAT, EDC/NHS or anhydrides may be employed to similar effect.

Urea and Thiourea Formation:

Isocyanates and thioisocyanates may be purchased or prepared by reaction of the corresponding amine with triphosgene, diphosgene, phosgene or thiophosgene as appropriate according to standard procedures as outlined in "Organic Functional Group Preparation" Vol I, $2^{nd}$ Ed., Sandier and Karo, Academic Press, ISBN:0-126186014 pp 359 to 375.

Resin bound building block which has previously had an amine group deprotected is suspended in anhydrous THF and 2 equivalents of the isocyanate or thioisocyanate added, followed immediately by triethylamine (1 equivalent). The mixture is shaken for 2 hours and may be exothermic depending on the scale and reactivity of the isocyanate or thioisocyanate used, drained and re-treated with fresh reagents for a further 2 hours. The resin is filtered, washed with THF followed by methanol and finally dichloromethane.

Carbamate Formation:

Chloroformates and imidoylformates may be purchased or prepared by reaction of the corresponding alcohol with phosgene or carbonylbisimidazole as appropriate according to standard procedures as outlined in "Organic Functional Group Preparation" Vol I, $2^{nd}$ Ed., Sandier and Karo, Academic Press, ISBN:0-12-6186014 pp 359 to 375.

Resin bound building block which has previously had an amine group deprotected is suspended in anhydrous THF and 2 equivalents of the chloroformate or imidoylformate added, followed immediately by triethylamine (1 equivalent). The mixture is shaken for 2 hours and may be exothermic depending on the scale and reactivity of the isocyanate or thioisocyanate used, drained and retreated with fresh reagents for a further 2 hours. The resin is filtered, washed with THF followed by methanol and finally dichloromethane.

Sulfonamide Formation:

Resin bound building block which has previously had an amine group deprotected is suspended in anhydrous THF or DMF and 2 equivalents of the sulfonyl chloride added, followed immediately by triethylamine (2 equivalent). The mixture is shaken for 2 hours, drained and retreated with fresh reagents for a further 2 hours. The resin is filtered, washed with THF or DMF followed by methanol and finally dichloromethane.

Removal of Fmoc:

The resin bound building block is suspended in piperidine/DMF (1/4, v/v) mixture and stirred 1 hours, drained and repeated once more; the resin is filtered, washed with dimethylformamide followed by THF and finally dichloromethane.

Guanidine Formation:

The resin bound building block is suspended in dry DMF containing 3 equivalents of 3,5-dimethylpyrazolyl formamidinium nitrate and 15 equivalents of DIPEA. The mixture is stirred at 65° C. for 24 hours, drained; the resin is filtered, washed with dimethylformamide followed by THF and finally dichloromethane.

Cleavage of Resin Bound Product:

The resin bound compound is suspended in dry DCM containing 20% TFA and 20% $Et_3SiH$. The mixture is stirred at RT for 3 hours and the aliquot was collected; the resin was washed with dry DCM and all the DCM solutions were combined, evaporated to dryness under reduced vacuo to furnish the desired product.

Libraries of compounds of the invention have been prepared based on the following scaffolds:

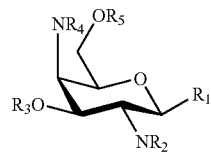
Scaffold W1 derived from A-6

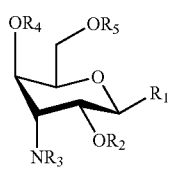
Scaffold W2 derived from B-4 or K-8

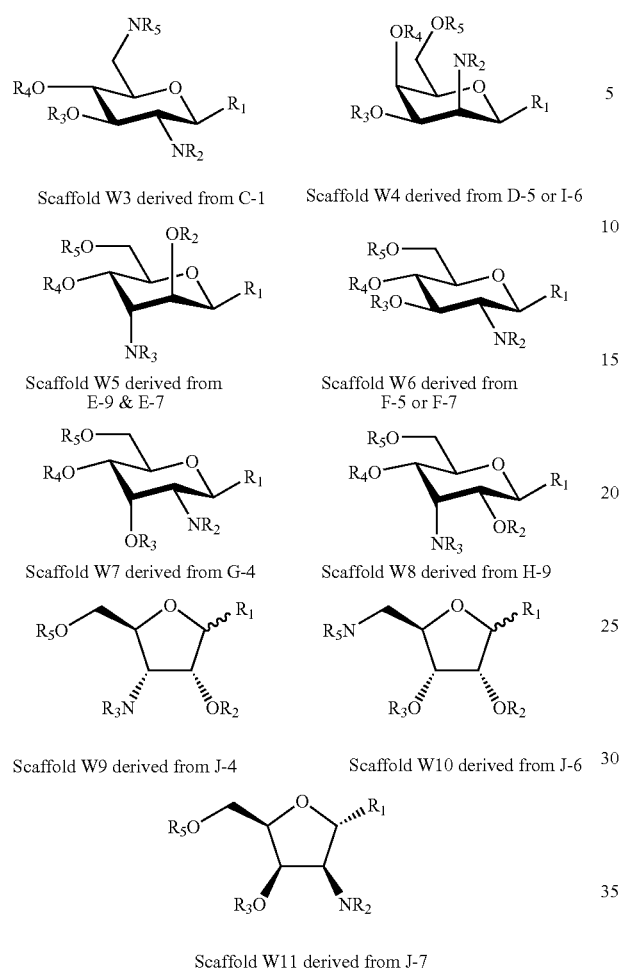

Scaffold W3 derived from C-1
Scaffold W4 derived from D-5 or I-6
Scaffold W5 derived from E-9 & E-7
Scaffold W6 derived from F-5 or F-7
Scaffold W7 derived from G-4
Scaffold W8 derived from H-9
Scaffold W9 derived from J-4
Scaffold W10 derived from J-6

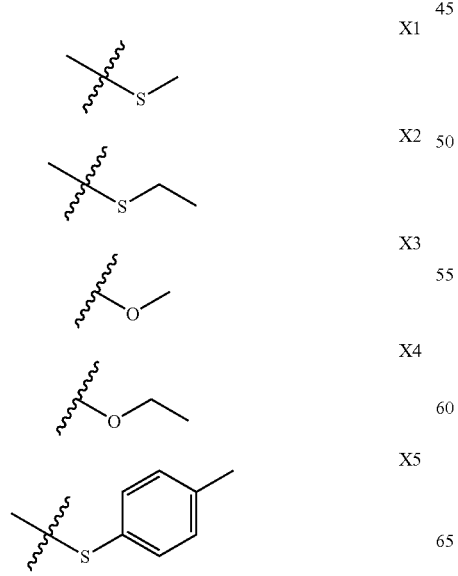

Scaffold W11 derived from J-7

The following groups are exemplary of moieties in position R1, where the wavey line indicates the point of attachment to the carbohydrate ring:

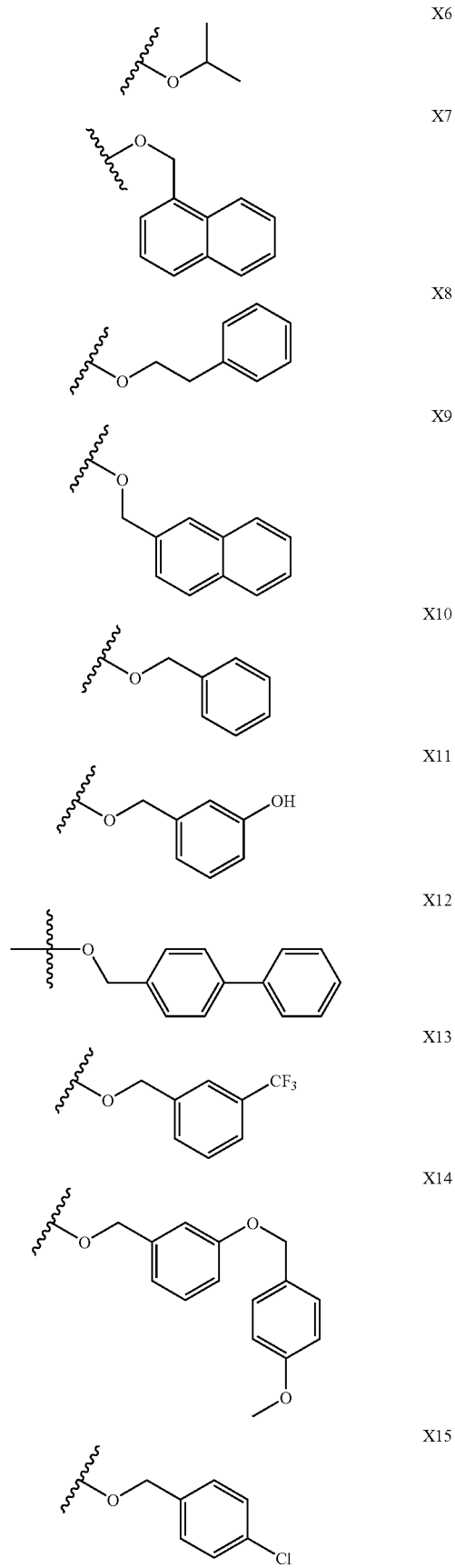

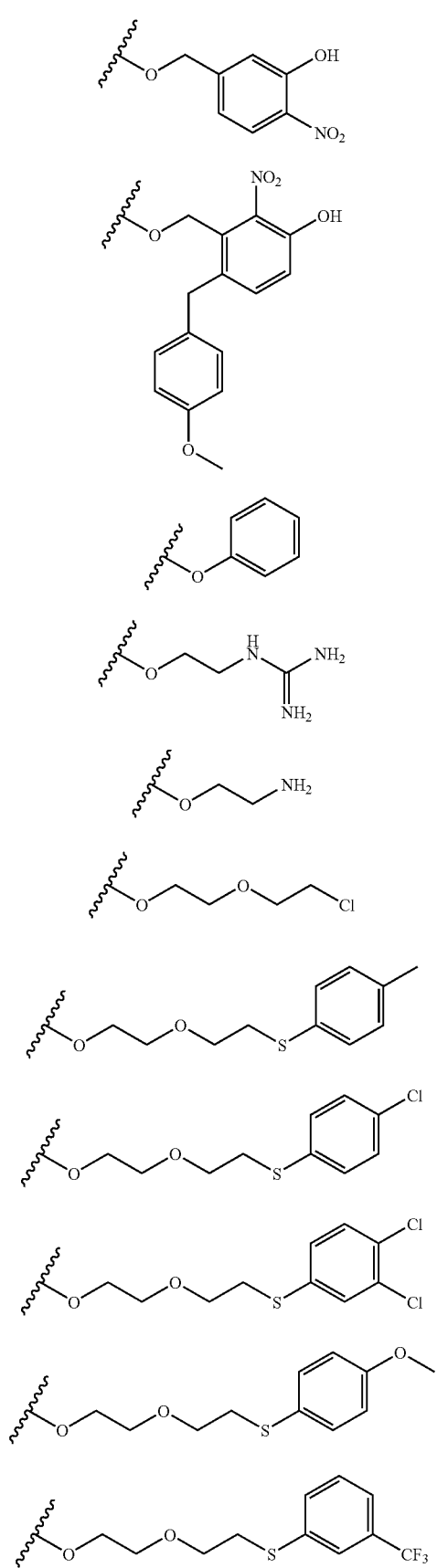
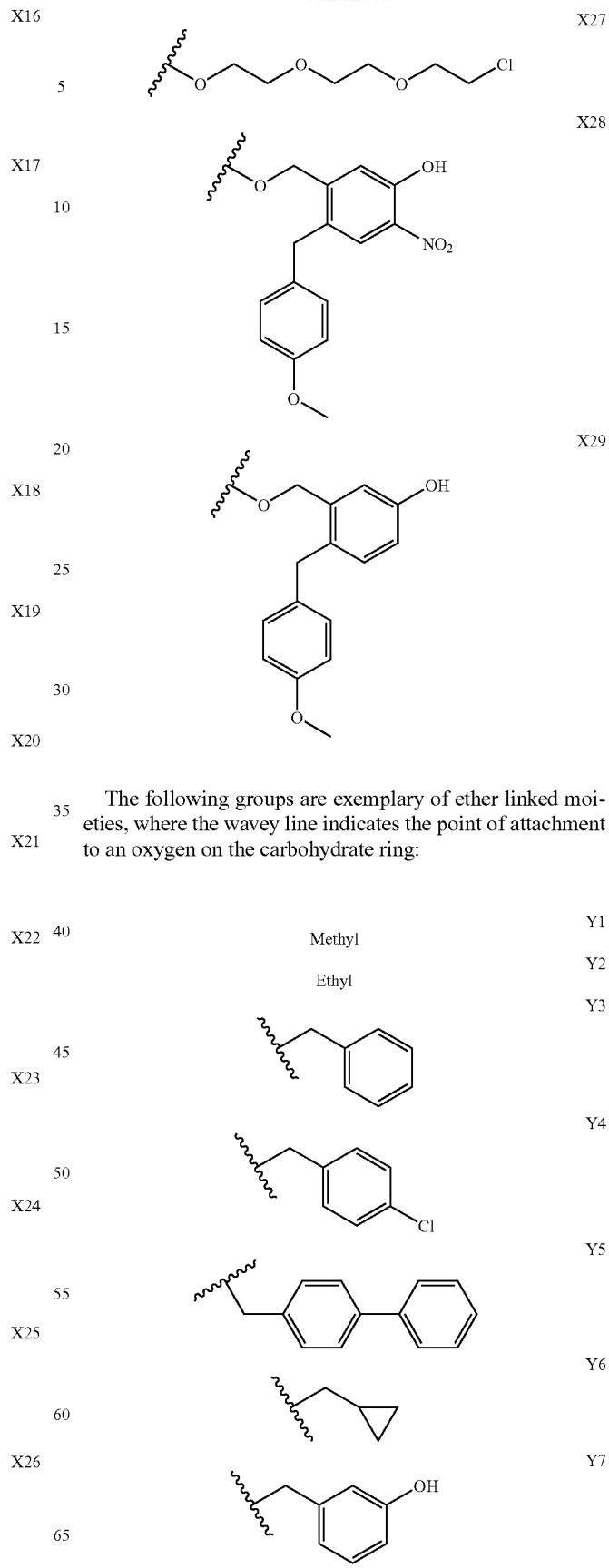
The following groups are exemplary of ether linked moieties, where the wavey line indicates the point of attachment to an oxygen on the carbohydrate ring:
Y1  Methyl
Y2  Ethyl

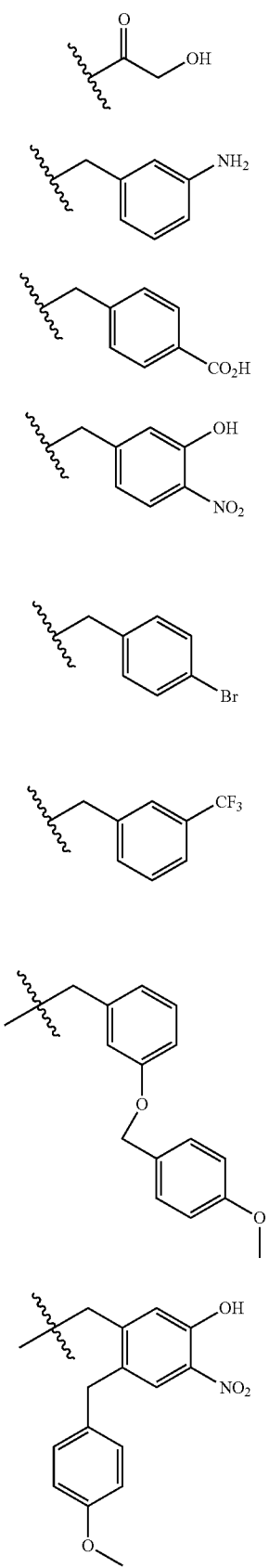
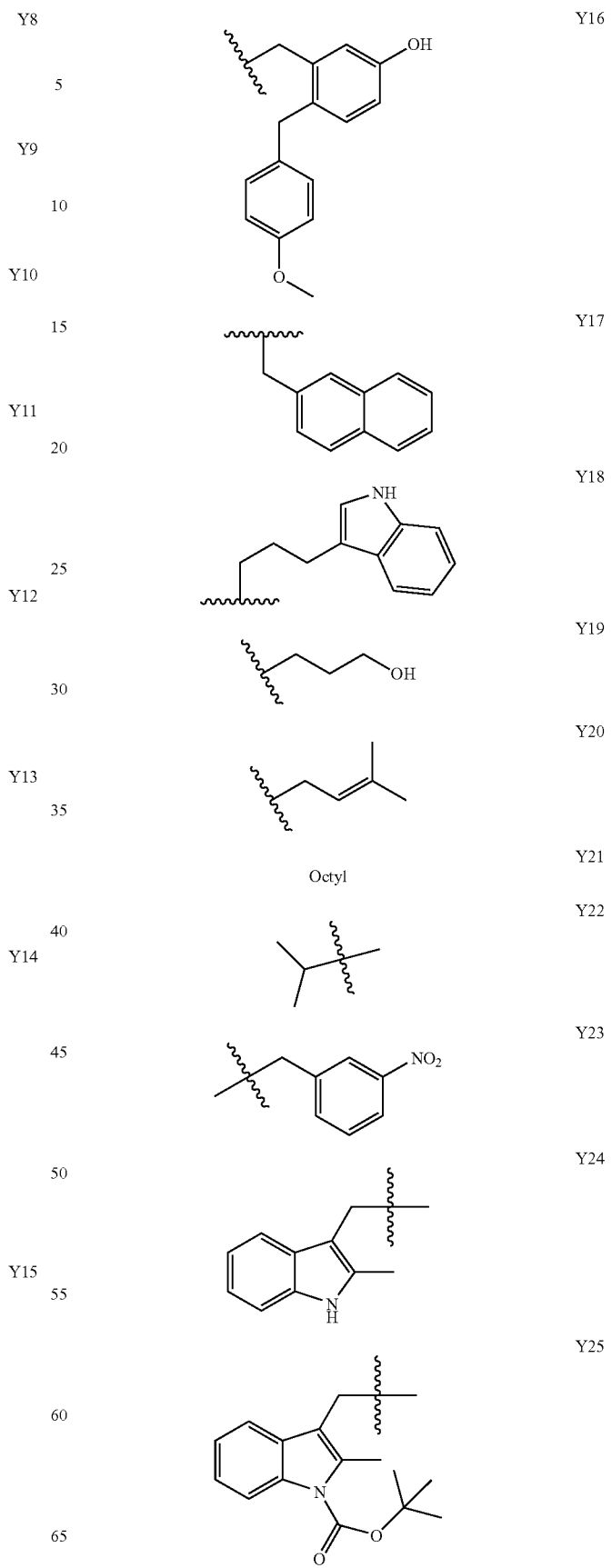

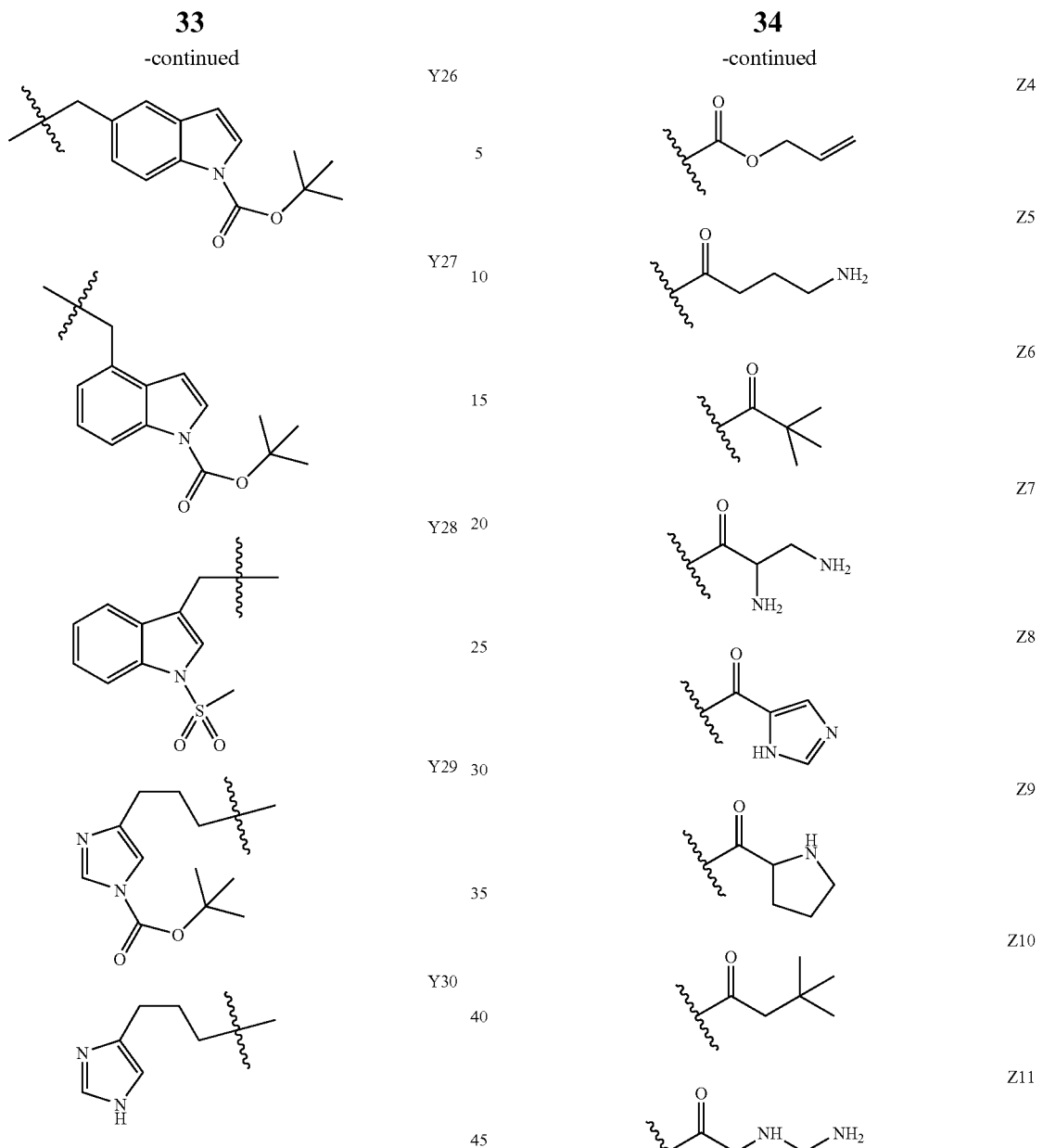
The following groups are exemplary of amine linked moieties, where the wavey line indicates the point of attachment to a nitrogen on the carbohydrate ring:
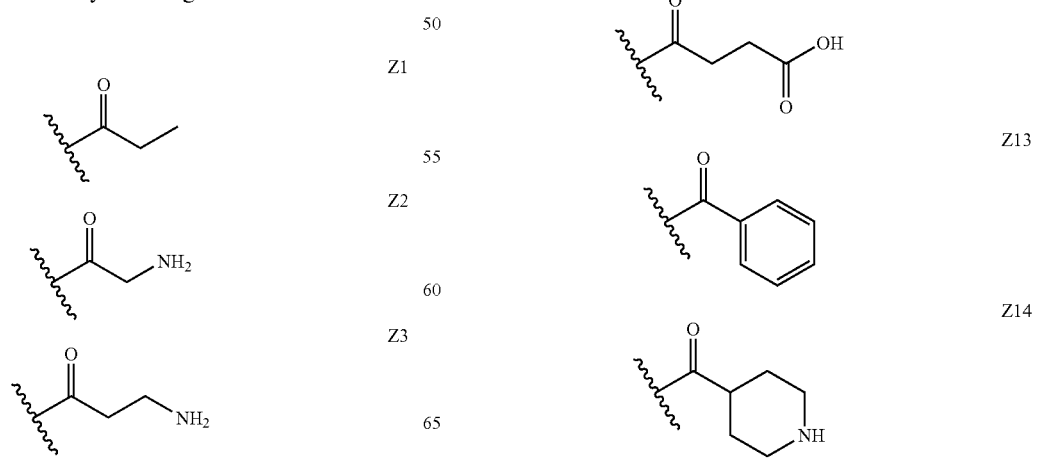

-continued
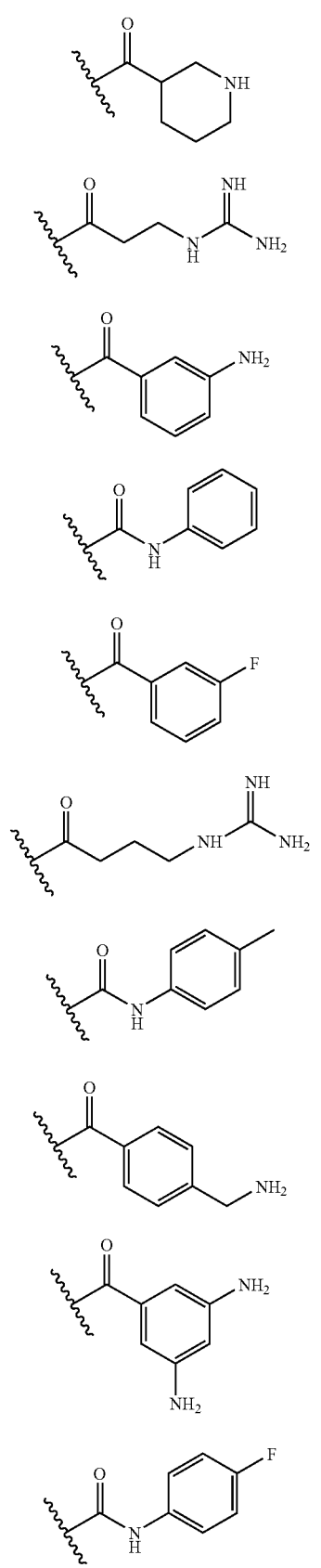
Z15
Z16
Z17
Z18
Z19
Z20
Z21
Z22
Z23
Z24
-continued
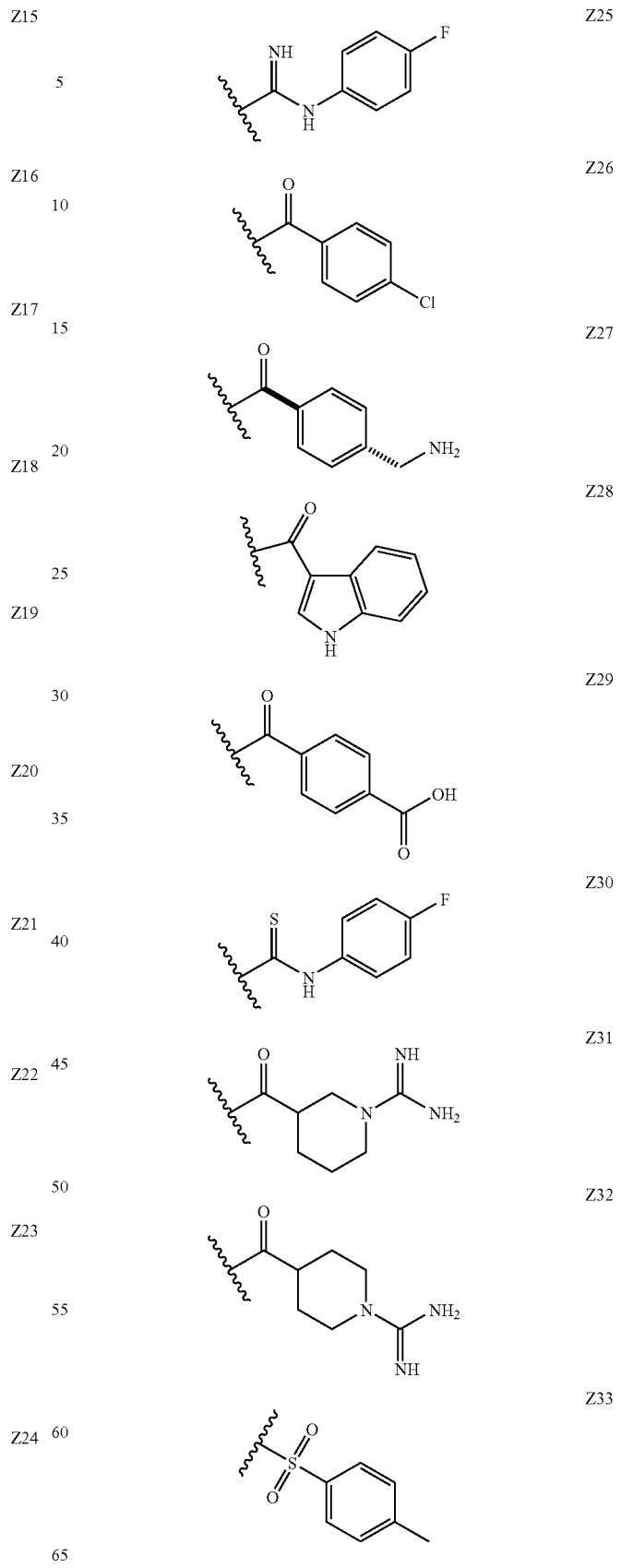
Z25
Z26
Z27
Z28
Z29
Z30
Z31
Z32
Z33

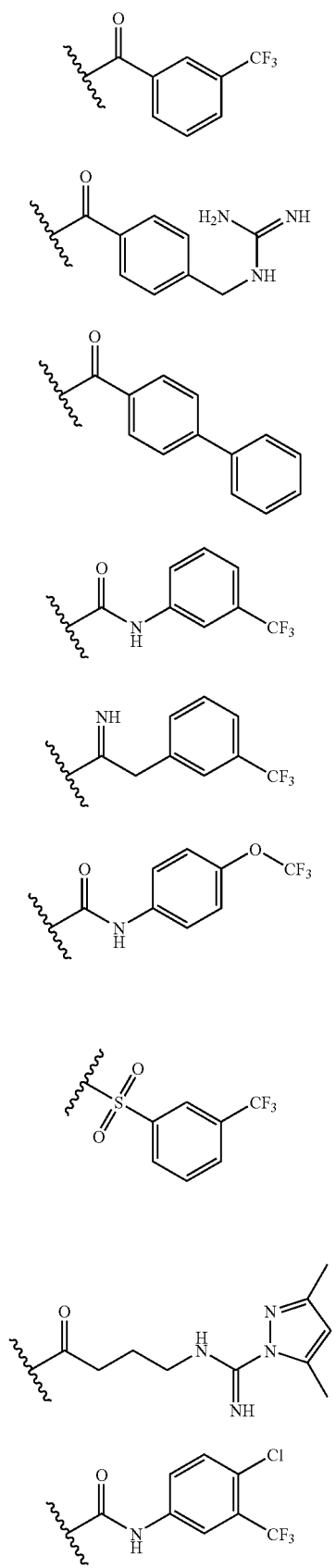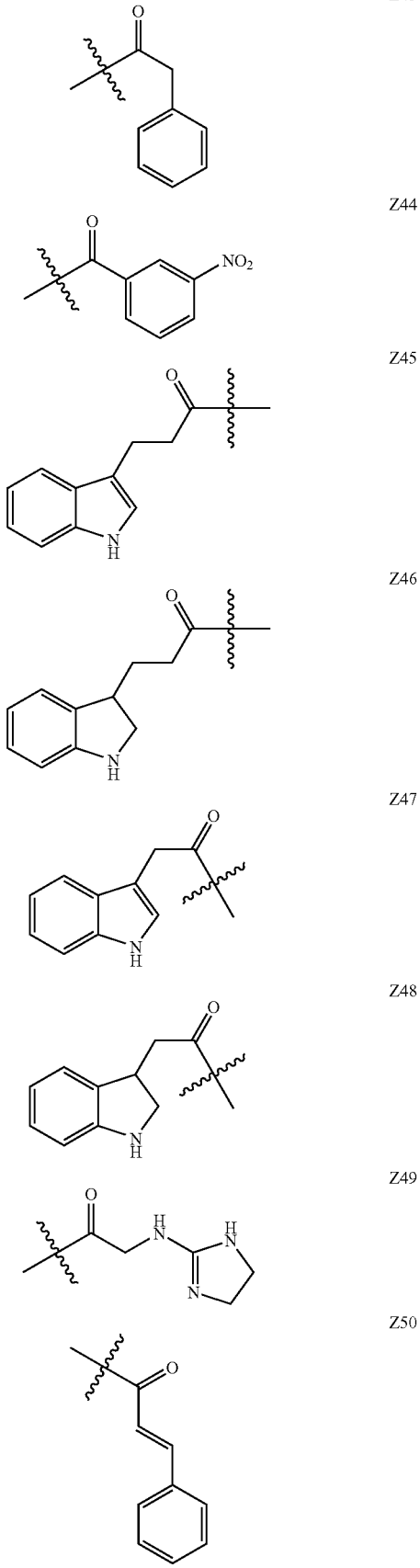

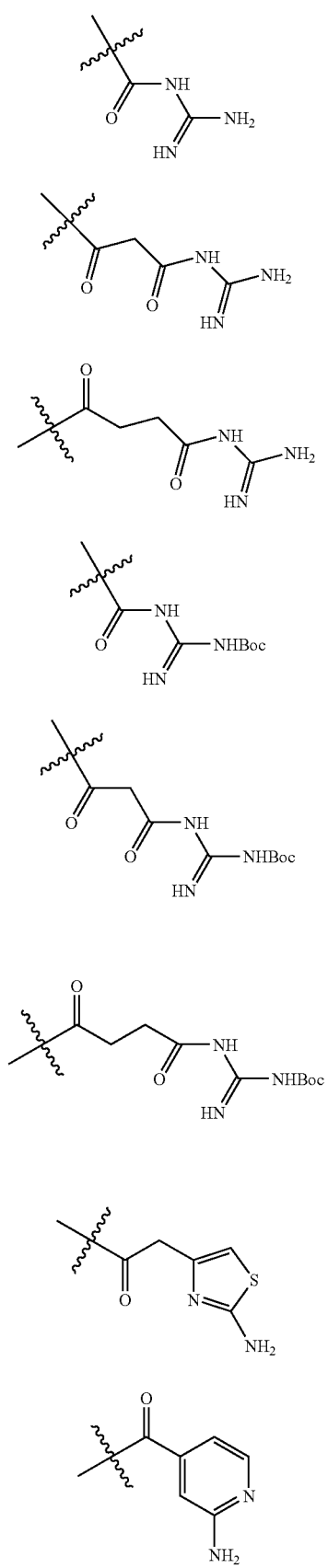

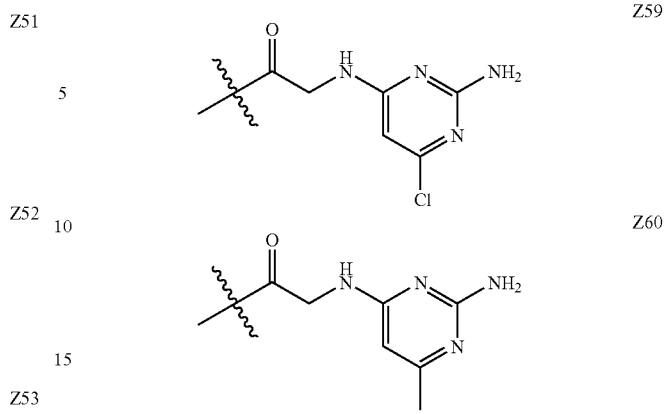

Exemplary library compounds:

| Compound Number | Scaffold | R1 | R2 | R3 | R4 | R5 |
|---|---|---|---|---|---|---|
| 1 | W6 | X1 | Z43 | Y3 | H | Y21 |
| 2 | W6 | X1 | Z44 | Y3 | H | Y22 |
| 3 | W6 | X1 | Z45 | Y3 | H | Y23 |
| 4 | W6 | X1 | Z46 | Y3 | H | Y24 |
| 5 | W6 | X1 | Z47 | Y3 | H | Y25 |
| 6 | W6 | X1 | Z48 | Y3 | H | Y26 |
| 7 | W6 | X1 | Z49 | Y3 | H | Y27 |
| 8 | W6 | X1 | Z50 | Y3 | H | Y28 |
| 9 | W6 | X1 | Z51 | Y3 | H | Y29 |
| 10 | W6 | X1 | Z52 | Y3 | H | Y30 |
| 11 | W6 | X1 | Z53 | Y3 | H | Y21 |
| 12 | W6 | X1 | Z54 | Y3 | H | Y22 |
| 13 | W6 | X1 | Z55 | Y3 | H | Y23 |
| 14 | W6 | X1 | Z56 | Y3 | H | Y24 |
| 15 | W6 | X1 | Z57 | Y3 | H | Y25 |
| 16 | W6 | X1 | Z58 | Y3 | H | Y26 |
| 17 | W6 | X1 | Z59 | Y3 | H | Y27 |
| 18 | W6 | X1 | Z60 | Y3 | H | Y28 |
| 19 | W6 | X3 | Z12 | Y9 | H | Y29 |
| 20 | W6 | X3 | Z29 | Y9 | H | Y30 |
| 21 | W6 | X3 | Z12 | Y9 | H | Y12 |
| 22 | W6 | X3 | Z29 | Y9 | H | Y12 |
| 23 | W6 | X3 | Z13 | Y9 | H | Y8 |
| 24 | W6 | X3 | Z26 | Y9 | H | Y8 |
| 25 | W6 | X3 | Z13 | Y3 | H | Y10 |
| 26 | W6 | X3 | Z26 | Y3 | H | Y10 |
| 27 | W6 | X4 | Z3 | Y3 | H | Y8 |
| 28 | W6 | X4 | Z17 | Y3 | H | Y8 |
| 29 | W6 | X4 | Z3 | Y3 | H | Y10 |
| 30 | W6 | X4 | Z17 | Y3 | H | Y10 |
| 31 | W6 | X4 | Z12 | Y3 | H | Y9 |
| 32 | W6 | X4 | Z29 | Y3 | H | Y9 |
| 33 | W6 | X4 | Z3 | Y12 | H | Y8 |
| 34 | W6 | X4 | Z17 | Y12 | H | Y8 |
| 35 | W6 | X4 | Z3 | Y12 | H | Y10 |
| 36 | W6 | X4 | Z17 | Y12 | H | Y10 |
| 37 | W6 | X4 | Z12 | Y12 | H | Y9 |
| 38 | W6 | X4 | Z29 | Y12 | H | Y9 |
| 39 | W6 | X4 | Z3 | Y8 | H | Y3 |
| 40 | W6 | X4 | Z17 | Y8 | H | Y3 |
| 41 | W6 | X4 | Z3 | Y8 | H | Y12 |
| 42 | W6 | X4 | Z17 | Y8 | H | Y12 |
| 43 | W6 | X4 | Z13 | Y8 | H | Y9 |
| 44 | W6 | X4 | Z26 | Y8 | H | Y9 |
| 45 | W6 | X4 | Z3 | Y10 | H | Y3 |
| 46 | W6 | X4 | Z17 | Y10 | H | Y3 |
| 47 | W6 | X4 | Z3 | Y10 | H | Y12 |
| 48 | W6 | X4 | Z17 | Y10 | H | Y12 |
| 49 | W6 | X4 | Z13 | Y10 | H | Y9 |
| 50 | W6 | X4 | Z26 | Y10 | H | Y9 |
| 51 | W6 | X4 | Z12 | Y9 | H | Y3 |
| 52 | W6 | X4 | Z29 | Y9 | H | Y3 |
| 53 | W6 | X4 | Z12 | Y9 | H | Y12 |

| Compound Number | Scaffold | R1 | R2 | R3 | R4 | R5 |
|---|---|---|---|---|---|---|
| 54 | W6 | X4 | Z29 | Y9 | H | Y12 |
| 55 | W6 | X4 | Z13 | Y9 | H | Y9 |
| 56 | W6 | X4 | Z26 | Y9 | H | Y9 |
| 57 | W6 | X4 | Z13 | Y9 | H | Y10 |
| 58 | W6 | X4 | Z26 | Y9 | H | Y10 |
| 59 | W6 | X4 | Z3 | Y2 | H | Y8 |
| 60 | W6 | X4 | Z17 | Y2 | H | Y8 |
| 61 | W6 | X4 | Z3 | Y2 | H | Y10 |
| 62 | W6 | X4 | Z17 | Y2 | H | Y10 |
| 63 | W6 | X4 | Z12 | Y2 | H | Y9 |
| 64 | W6 | X4 | Z29 | Y2 | H | Y9 |
| 65 | W6 | X4 | Z3 | Y8 | H | Y1 |
| 66 | W6 | X10 | Z17 | Y8 | H | Y1 |
| 67 | W6 | X10 | Z3 | Y8 | H | Y2 |
| 68 | W6 | X10 | Z17 | Y8 | H | Y2 |
| 69 | W6 | X10 | Z1 | Y8 | H | Y9 |
| 70 | W6 | X10 | Z4 | Y8 | H | Y9 |
| 71 | W6 | X10 | Z3 | Y10 | H | Y1 |
| 72 | W6 | X10 | Z17 | Y10 | H | Y1 |
| 73 | W6 | X10 | Z3 | Y10 | H | Y2 |
| 74 | W6 | X10 | Z17 | Y10 | H | Y2 |
| 75 | W6 | X10 | Z1 | Y10 | H | Y9 |
| 76 | W6 | X10 | Z4 | Y10 | H | Y9 |
| 77 | W6 | X10 | Z12 | Y9 | H | Y1 |
| 78 | W6 | X10 | Z29 | Y9 | H | Y1 |
| 79 | W6 | X10 | Z12 | Y9 | H | Y2 |
| 80 | W6 | X10 | Z29 | Y9 | H | Y2 |
| 81 | W6 | X10 | Z1 | Y9 | H | Y9 |
| 82 | W6 | X10 | Z4 | Y9 | H | Y9 |
| 83 | W6 | X15 | Z11 | Y1 | H | Y17 |
| 84 | W6 | X15 | Z4 | Y9 | H | Y10 |
| 85 | W8 | X6 | Y8 | Z33 | H | Y9 |
| 86 | W8 | X6 | Y10 | Z24 | H | Y19 |
| 87 | W8 | X6 | Y7 | Z18 | H | Y12 |
| 88 | W8 | X9 | Y9 | Z25 | H | Y3 |
| 89 | W8 | X9 | Y19 | Z1 | H | Y4 |
| 90 | W8 | X9 | Y12 | Z20 | H | Y13 |
| 91 | W8 | X12 | Y3 | Z25 | H | Y17 |
| 92 | W8 | X12 | Y4 | Z20 | H | Y11 |
| 93 | W8 | X12 | Y13 | Z20 | H | Y18 |
| 94 | W8 | X10 | Y17 | Z36 | H | Y8 |
| 95 | W8 | X10 | Y11 | Z42 | H | Y10 |
| 96 | W8 | X10 | Y18 | Z18 | H | Y13 |
| 97 | W1 | X6 | Z33 | Y4 | Z37 | H |
| 98 | W1 | X6 | Z37 | H | Z33 | Y3 |
| 99 | W1 | X6 | Z42 | H | Z18 | Y3 |
| 100 | W1 | X9 | Z33 | Y4 | Z37 | H |
| 101 | W1 | X9 | Z37 | H | Z33 | Y3 |
| 102 | W1 | X9 | Z42 | H | Z18 | Y3 |
| 103 | W1 | X12 | Z33 | Y4 | Z37 | H |
| 104 | W1 | X12 | Z37 | H | Z33 | Y3 |
| 105 | W1 | X12 | Z42 | H | Z18 | Y3 |
| 106 | W6 | X12 | Z11 | Y5 | H | Y1 |
| 107 | W6 | X12 | Z16 | Y5 | H | Y1 |
| 108 | W6 | X12 | Z5 | Y5 | H | Y1 |
| 109 | W6 | X12 | Z11 | Y17 | H | Y1 |
| 110 | W6 | X12 | Z16 | Y17 | H | Y1 |
| 111 | W6 | X12 | Z5 | Y17 | H | Y1 |
| 112 | W6 | X12 | Z11 | Y3 | H | Y1 |
| 113 | W6 | X12 | Z16 | Y3 | H | Y1 |
| 114 | W6 | X12 | Z5 | Y3 | H | Y1 |
| 115 | W6 | X12 | Z11 | Y4 | H | Y1 |
| 116 | W6 | X12 | Z16 | Y4 | H | Y1 |
| 117 | W6 | X12 | Z5 | Y4 | H | Y1 |
| 118 | W6 | X9 | Z11 | Y5 | H | Y1 |
| 119 | W6 | X9 | Z16 | Y5 | H | Y1 |
| 120 | W6 | X9 | Z5 | Y5 | H | Y1 |
| 121 | W6 | X9 | Z11 | Y17 | H | Y1 |
| 122 | W6 | X9 | Z16 | Y17 | H | Y1 |
| 123 | W6 | X9 | Z5 | Y17 | H | Y1 |
| 124 | W6 | X9 | Z11 | Y3 | H | Y1 |
| 125 | W6 | X9 | Z16 | Y3 | H | Y1 |
| 126 | W6 | X9 | Z5 | Y3 | H | Y1 |
| 127 | W6 | X9 | Z11 | Y4 | H | Y1 |
| 128 | W6 | X9 | Z16 | Y4 | H | Y1 |
| 129 | W6 | X9 | Z5 | Y4 | H | Y1 |
| 130 | W6 | X12 | Z11 | Y1 | H | Y5 |
| 131 | W6 | X12 | Z16 | Y1 | H | Y5 |
| 132 | W6 | X12 | Z5 | Y1 | H | Y5 |
| 133 | W6 | X19 | Z28 | Y1 | H | Y3 |
| 134 | W6 | X19 | Z13 | Y1 | H | Y17 |
| 135 | W6 | X19 | Z13 | Y17 | H | Y1 |
| 136 | W6 | X3 | Z29 | Y12 | H | Y9 |
| 137 | W6 | X3 | Z17 | Y8 | H | Y3 |
| 138 | W6 | X3 | Z17 | Y8 | H | Y12 |
| 139 | W7 | X12 | Z11 | Y11 | H | Y1 |
| 140 | W7 | X12 | Z16 | Y15 | H | Y1 |
| 141 | W7 | X12 | Z3 | Y16 | H | Y1 |
| 142 | W7 | X8 | Z11 | Y11 | H | Y1 |
| 143 | W7 | X8 | Z16 | Y15 | H | Y1 |
| 145 | W7 | X8 | Z3 | Y16 | H | Y1 |
| 146 | W7 | X15 | Z11 | Y11 | H | Y1 |
| 147 | W7 | X15 | Z16 | Y15 | H | Y1 |
| 148 | W7 | X15 | Z3 | Y16 | H | Y1 |
| 149 | W7 | X17 | Z17 | Y4 | H | Y1 |
| 150 | W7 | X15 | Z7 | H | Y4 | Y17 |
| 151 | W7 | X15 | Z31 | H | Y4 | Y17 |
| 152 | W7 | X15 | Z9 | H | Y4 | Y17 |
| 153 | W7 | X15 | Z32 | H | Y4 | Y17 |
| 154 | W6 | X15 | Z42 | Y6 | Y1 | H |
| 155 | W6 | X15 | Z37 | Y20 | Y1 | H |
| 156 | W6 | X15 | Z39 | Y2 | Y1 | H |
| 157 | W6 | X14 | Z42 | Y6 | Y8 | H |
| 158 | W6 | X14 | Z37 | Y20 | Y8 | H |
| 159 | W6 | X6 | Z17 | Y8 | Y3 | H |
| 160 | W2 | X8 | H | Z13 | Y4 | Y1 |
| 161 | W2 | X8 | H | Z16 | Y4 | Y1 |
| 162 | W3 | X15 | Z36 | Y4 | H | Z37 |
| 163 | W3 | X5 | Z11 | Y4 | H | Z33 |
| 164 | W3 | X5 | Z8 | Y4 | H | Z24 |
| 165 | W3 | X5 | Z36 | Y4 | H | Z37 |
| 166 | W3 | X1 | Z11 | H | H | Z33 |
| 167 | W3 | X1 | Z8 | H | H | Z24 |
| 168 | W3 | X1 | Z36 | H | H | Z37 |
| 169 | W3 | X15 | Z11 | Y4 | H | Z33 |
| 170 | W3 | X15 | Z8 | Y4 | H | Z24 |
| 171 | W4 | X12 | Z10 | Y4 | Y8 | H |
| 172 | W4 | X12 | Z41 | Y8 | Y3 | H |
| 173 | W5 | X8 | Y17 | Z13 | Y4 | H |
| 174 | W5 | X8 | Y17 | Z16 | Y4 | H |
| 175 | W9 | X22 | Y4 | Z3 | Absent | H |
| 176 | W9 | X23 | Y5 | Z11 | Absent | H |
| 177 | W9 | X26 | Y8 | Z3 | Absent | H |
| 178 | W9 | X21 | Y17 | Z11 | Absent | H |
| 179 | W10 | X3 | Y6 | H | Absent | Z25 |
| 180 | W10 | X5 | Y12 | H | Absent | Z30 |
| 181 | W10 | X10 | Y19 | H | Absent | Z40 |
| 182 | W11 | X6 | Z25 | H | Absent | Y6 |
| 183 | W11 | X8 | Z30 | H | Absent | Y12 |
| 184 | W11 | X10 | Z40 | H | Absent | Y19 |

Exemplary synthesis of compound 85 W6-X15-Z11-Y1-OH-Y17) on solid phase.

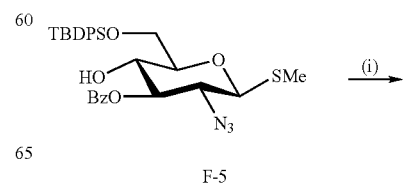

F-5

-continued

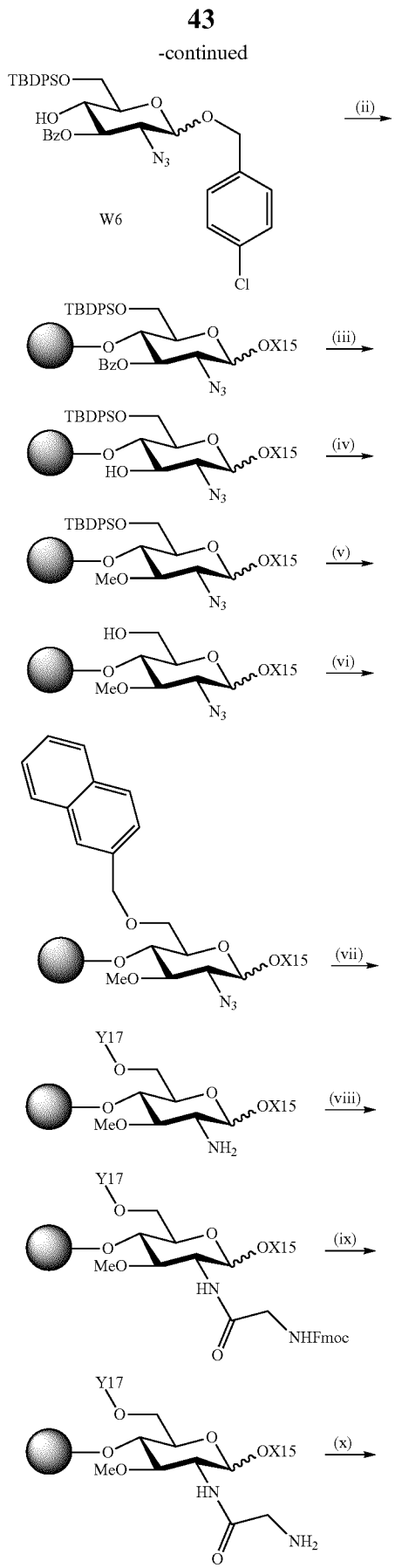

-continued

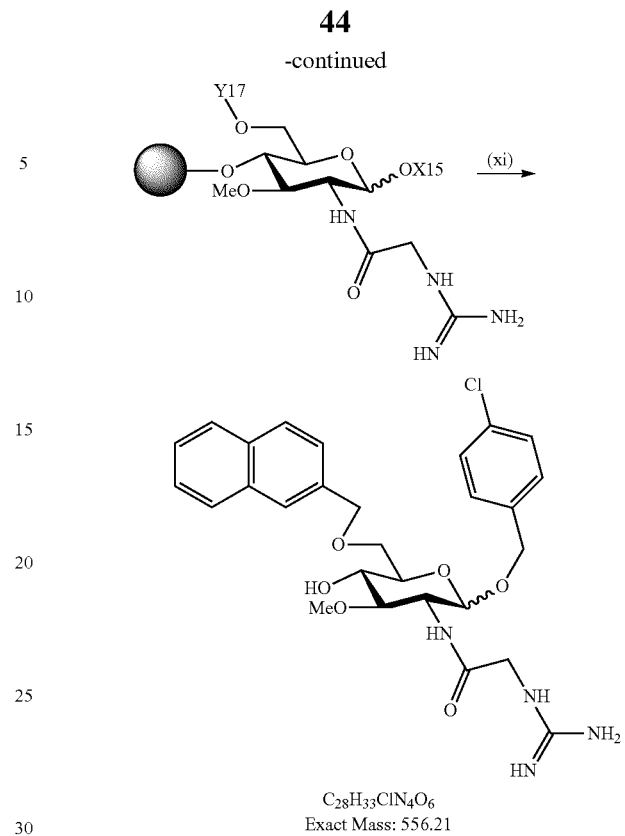

$C_{28}H_{33}ClN_4O_6$
Exact Mass: 556.21

Conditions: (i) a. $Br_2$, DCM; b. 4-Chlorobenzylalcohol, AgOTf, DCM; (ii) TCA-Wang resin, $BF_3.Et_2O$, DCM, THF; (iii) NaOMe, THF, MeOH; (iv) a. KOBu$^t$, DMF; b. iodomethane, DMF; (v) HF.'proton sponge', AcOH, DMF, 65° C.; (vi) a. KOBu$^t$, DMF; b. 2-bromomethyl-naphthalene, DMF; (vii) 1,4-Dithio-DL-threitol, KOBu$^t$, DMF; (viii) HBTU, Fmoc-Gly-OH, DIPEA, DMF; (ix) piperidine/DMF (¼); (x) 3,5dimethylpyrazolyl formamidinium nitrate, DIPEA, DMF; (xi) TFA, $Et_3SiH$, DCM.

LCMS Method:

| Time | water % | acetonitrile % | Flow (ml/min) |
|---|---|---|---|
| 0.00 | 95.0 | 5.0 | 2.000 |
| 1.00 | 95.0 | 5.0 | 2.000 |
| 7.00 | 0.0 | 100.0 | 2.000 |
| 12.00 | 0.0 | 100.0 | 2.000 |

M+H=557.3; Rt=3.98 min

Exemplary Synthesis of Compound 159 (W6-Z17-Y8-Y3OHA in Solution Phase:

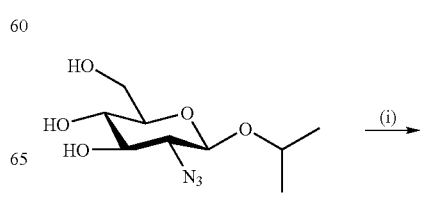

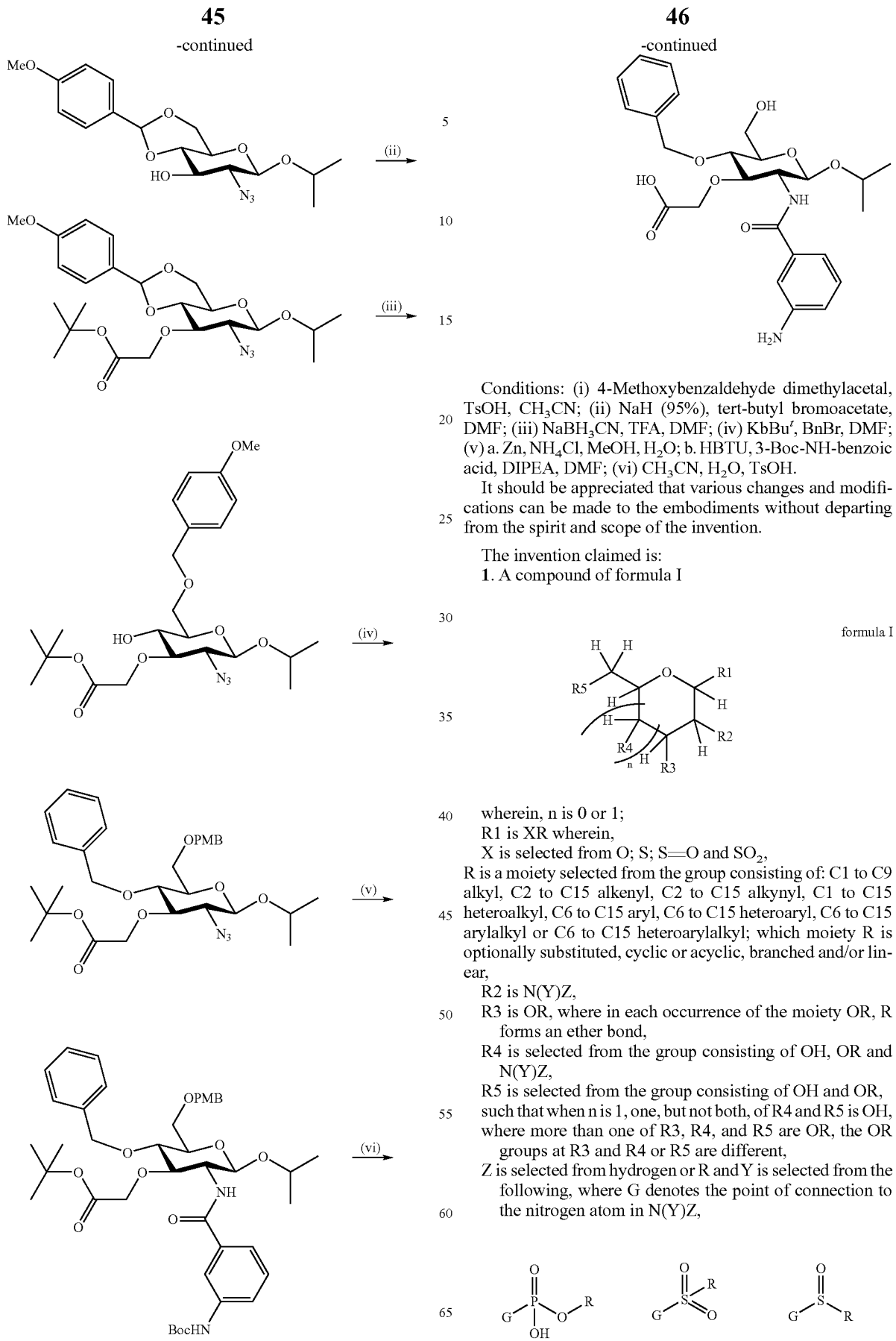

Conditions: (i) 4-Methoxybenzaldehyde dimethylacetal, TsOH, CH₃CN; (ii) NaH (95%), tert-butyl bromoacetate, DMF; (iii) NaBH₃CN, TFA, DMF; (iv) KbBu$^t$, BnBr, DMF; (v) a. Zn, NH₄Cl, MeOH, H₂O; b. HBTU, 3-Boc-NH-benzoic acid, DIPEA, DMF; (vi) CH₃CN, H₂O, TsOH.

It should be appreciated that various changes and modifications can be made to the embodiments without departing from the spirit and scope of the invention.

The invention claimed is:

1. A compound of formula I formula I wherein, n is 0 or 1;
R1 is XR wherein,
X is selected from O; S; S=O and SO₂,
R is a moiety selected from the group consisting of: C1 to C9 alkyl, C2 to C15 alkenyl, C2 to C15 alkynyl, C1 to C15 heteroalkyl, C6 to C15 aryl, C6 to C15 heteroaryl, C6 to C15 arylalkyl or C6 to C15 heteroarylalkyl; which moiety R is optionally substituted, cyclic or acyclic, branched and/or linear,
R2 is N(Y)Z,
R3 is OR, where in each occurrence of the moiety OR, R forms an ether bond,
R4 is selected from the group consisting of OH, OR and N(Y)Z,
R5 is selected from the group consisting of OH and OR,
such that when n is 1, one, but not both, of R4 and R5 is OH, where more than one of R3, R4, and R5 are OR, the OR groups at R3 and R4 or R5 are different,
Z is selected from hydrogen or R and Y is selected from the following, where G denotes the point of connection to the nitrogen atom in N(Y)Z,

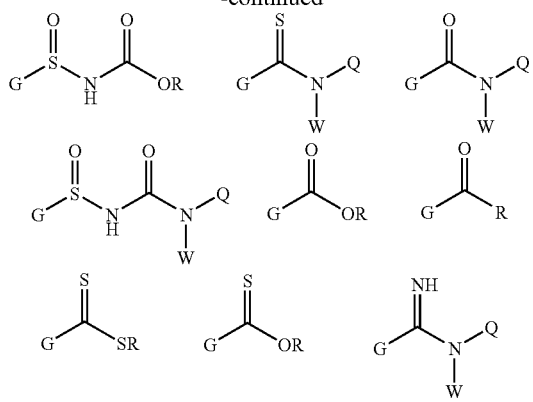

and the groups Q and W are independently selected from hydrogen or R as is defined above, and Q and W may combine to form a cycle, the groups Z and Y may combine to form a cycle, the groups R1 to R5 may not combine together to form a cycle, with the proviso that where two groups in the compound of formula I are N(Y)Z, these groups are different, with the further proviso that N(Y)Z may not be trifluoroacetamido, acetamido, with the further proviso that the group R may not be or contain another saccharide moiety; and wherein the optional substituents are selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, aminoaryl, aminoheteroaryl, thioalkyl, thioaryl or thioheteroaryl, which may be further substituted.

2. The compound of claim 1 wherein n is 1.

3. The compound of claim 2, wherein n is 1 and R4 is N(Z)Y.

4. A method of preparing a compound according to claim 1, wherein one step of said method comprises reduction of:

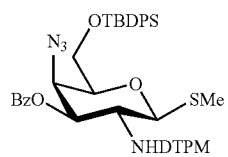

wherein $B_z$ is benzoyl, Me is methyl, TBDPS is t-butyldiphenylsilyl and DTPM is 5-acyl-1,3-dimethylbarbiturate.

5. A method of preparing a compound according to claim 1, wherein one step of said method comprises reduction of:

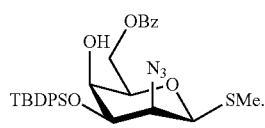

6. A method of preparing a compound according to claim 1, wherein one step of said method comprises reduction of:

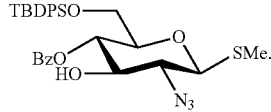

7. A method of preparing a compound according to claim 1, wherein one step of said method comprises reduction of:

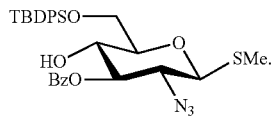

8. A method of preparing a compound according to claim 1, wherein one step of said method comprises reduction of:

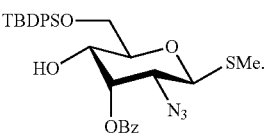

9. A method of preparing a compound according to claim 1, wherein one step of said method comprises reduction of:

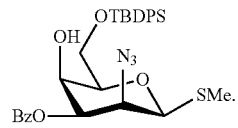

10. A method of preparing a compound according to claim 1, wherein one step of said method comprises reduction of:

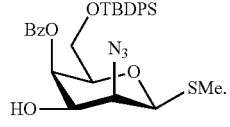

11. A method of preparing a compound according to claim 1, wherein one step of said method comprises reduction of:

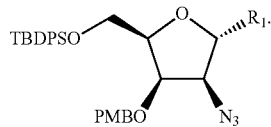

12. The compound according to claim 1 wherein the compound is immobilised to a support.

13. The compound according to claim 12, wherein the compound is immobilised to the support through a hydroxyl group.

14. The compound according to claim 13, wherein the support is selected from the group consisting of derivatised polystyrene, tentagel, wang resin, MBHA resin, aminomethylpolystyrene, rink amide resin, DOX-mpeg and polyethylene glycol.
15. The compound of claim 1, wherein R1 is selected from the group consisting of
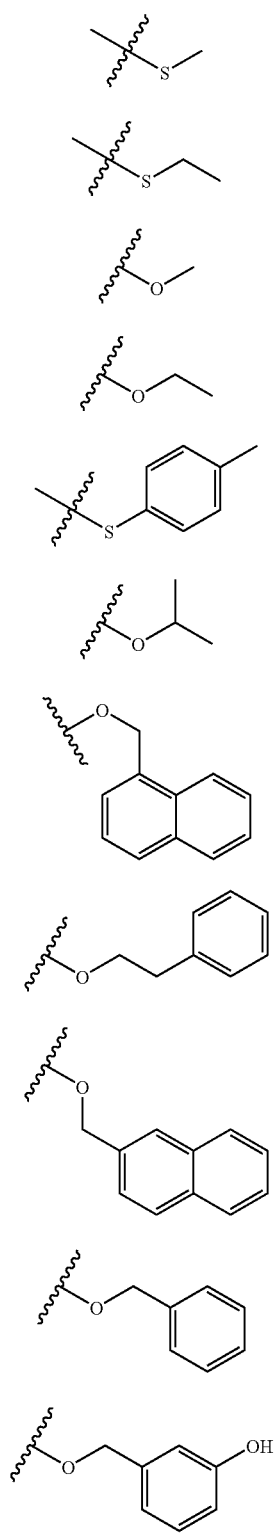
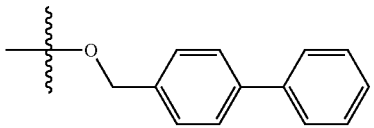
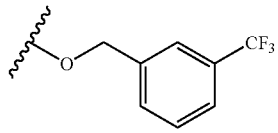
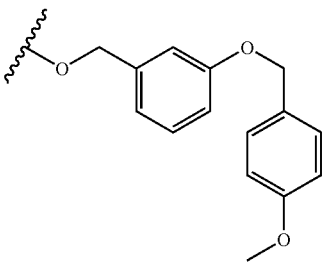
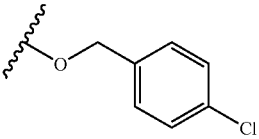
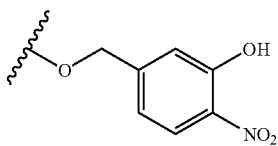
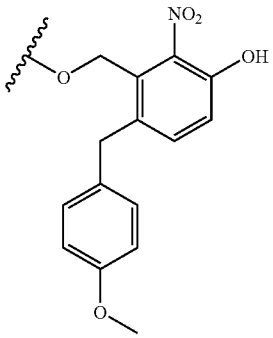
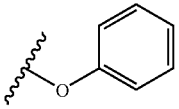
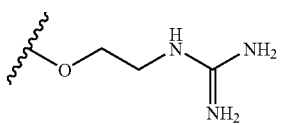
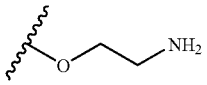
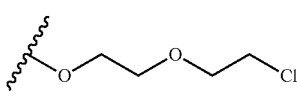

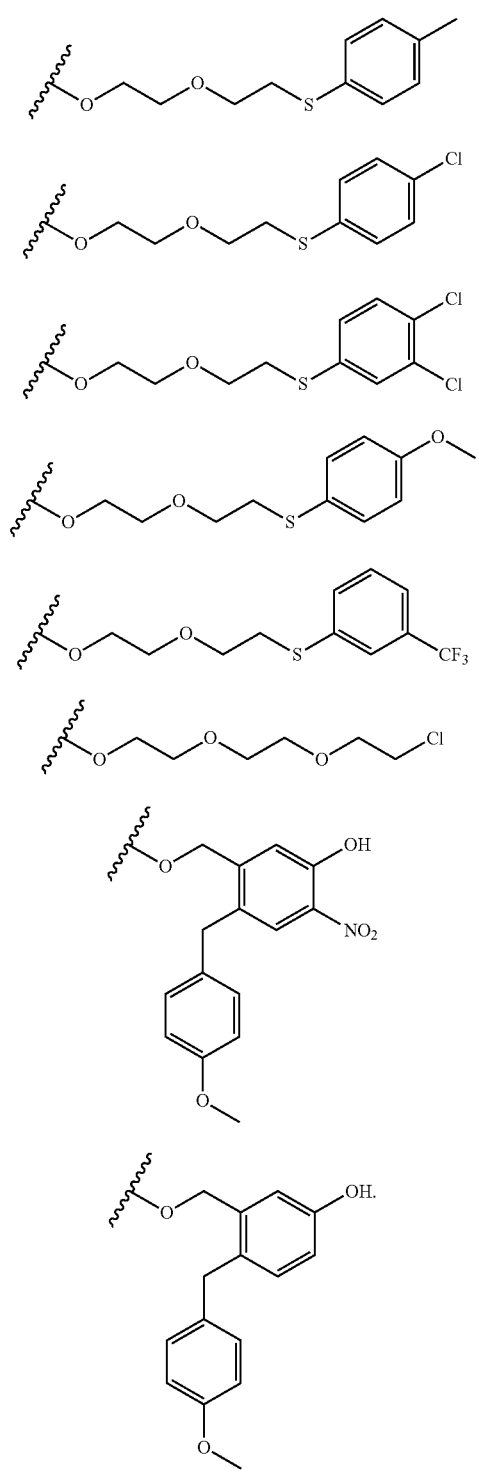
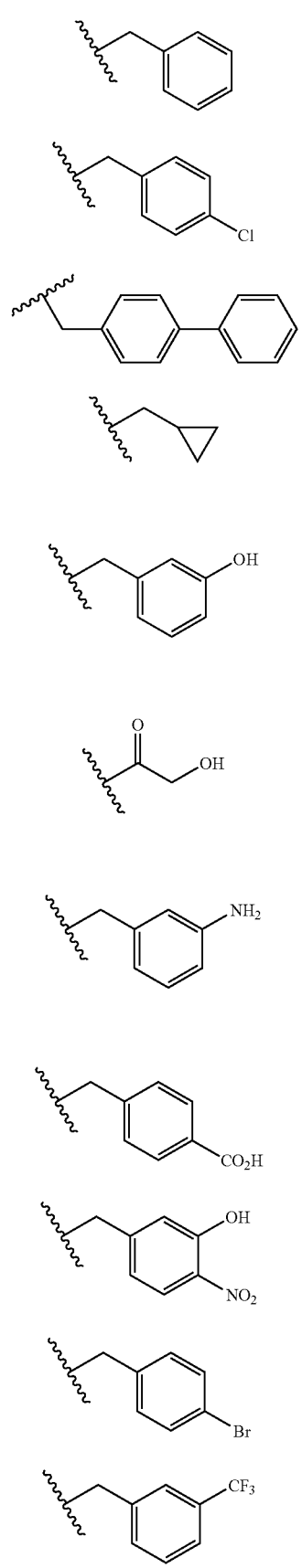
16. The compound of claim 1, wherein one of the R moieties in OR is selected from the group consisting of
Methyl Y1
Ethyl Y2

-continued
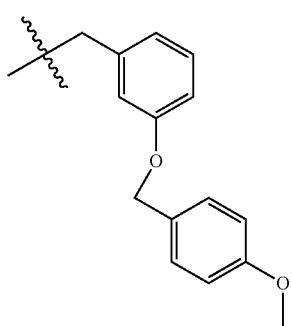 Y14
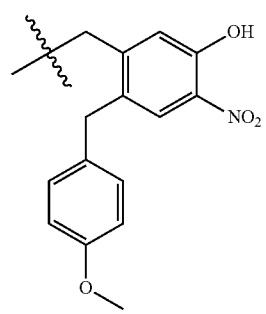 Y15
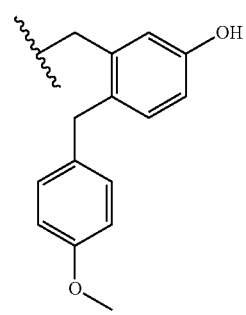 Y16
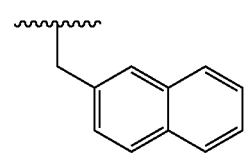 Y17
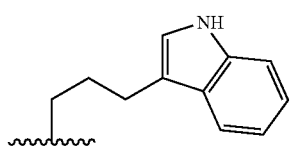 Y18
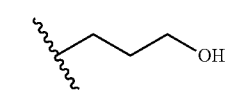 Y19
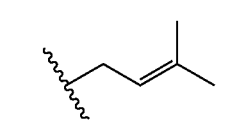 Y20
Octyl Y21
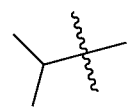 Y22
-continued
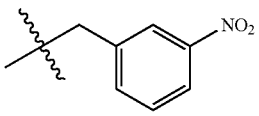 Y23
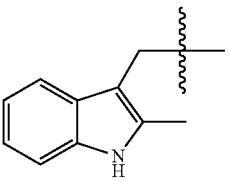 Y24
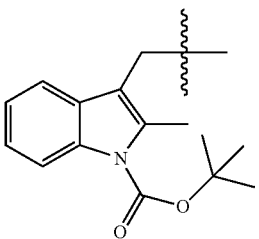 Y25
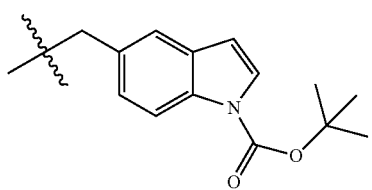 Y26
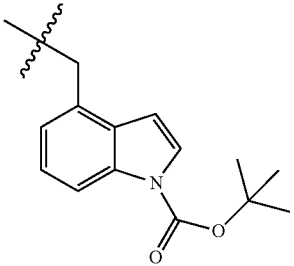 Y27
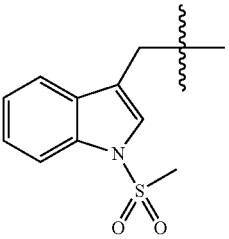 Y28
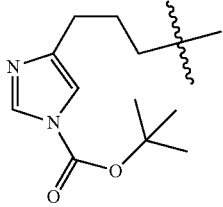 Y29

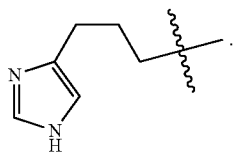 Y30
17. The compound of claim 1, wherein Y is selected from the group consisting of
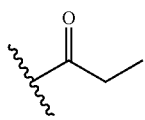 Z1
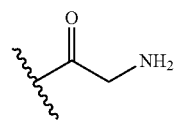 Z2
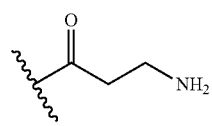 Z3
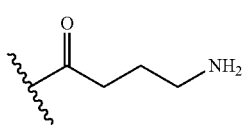 Z5
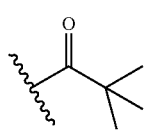 Z6
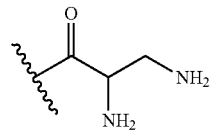 Z7
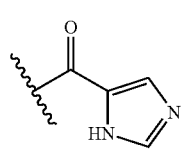 Z8
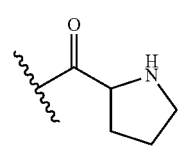 Z9
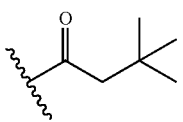 Z10
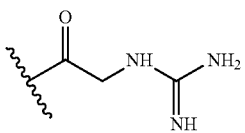 Z11
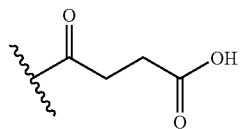 Z12
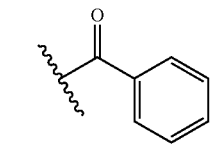 Z13
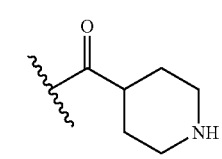 Z14
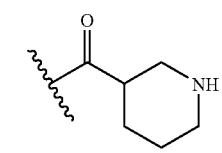 Z15
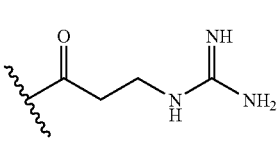 Z16
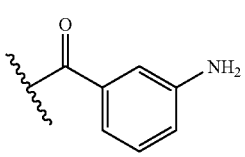 Z17
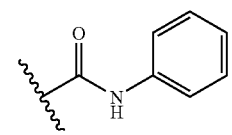 Z18
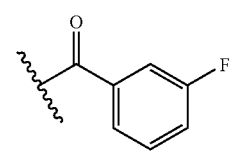 Z19
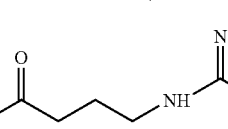 Z20
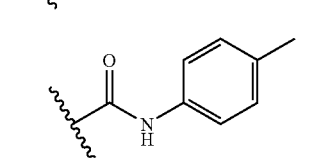 Z21

-continued
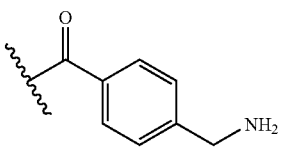 Z22
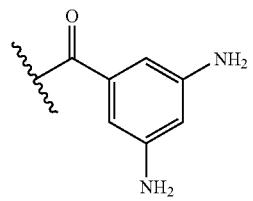 Z23
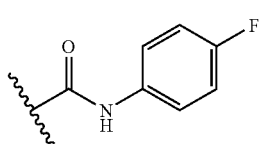 Z24
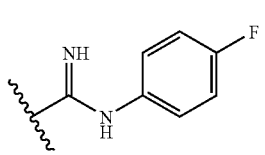 Z25
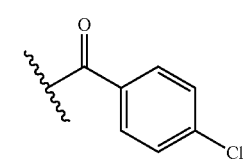 Z26
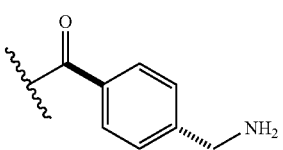 Z27
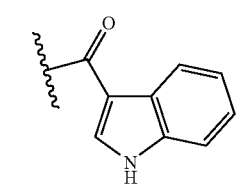 Z28
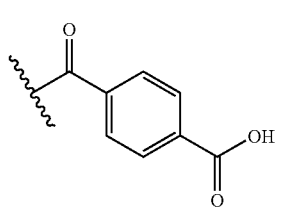 Z29
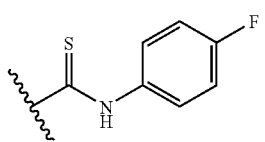 Z30
-continued
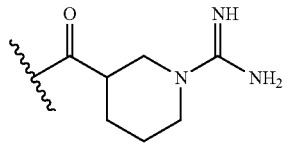 Z31
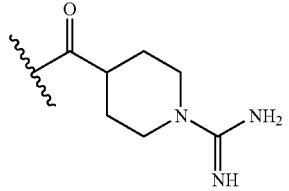 Z32
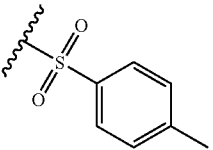 Z33
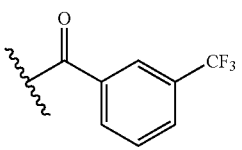 Z34
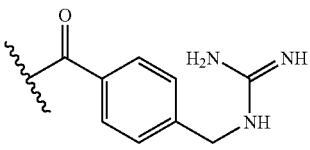 Z35
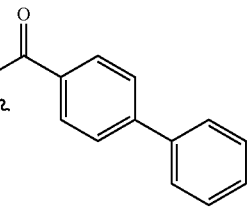 Z36
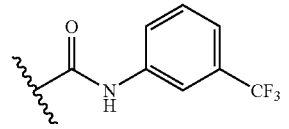 Z37
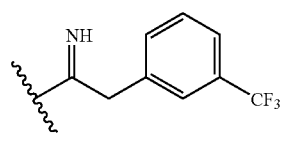 Z38
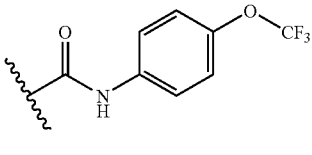 Z39
Z40

| | |
|---|---|
| 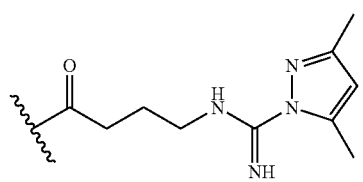 Z41 | 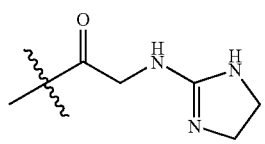 Z49 |
| 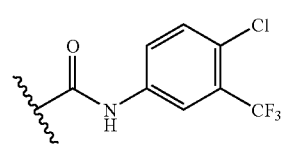 Z42 | 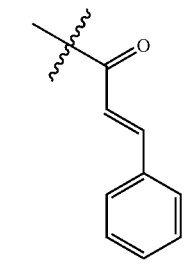 Z50 |
| 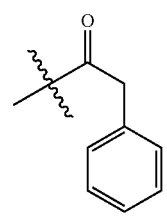 Z43 | |
| 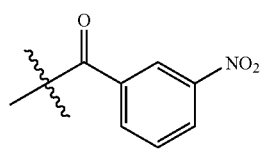 Z44 | 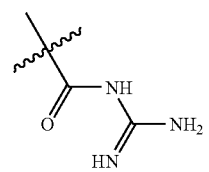 Z51 |
| 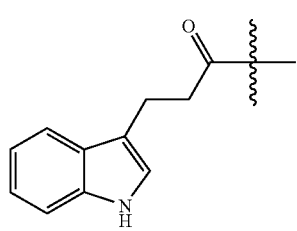 Z45 | 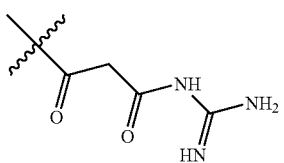 Z52 |
| | 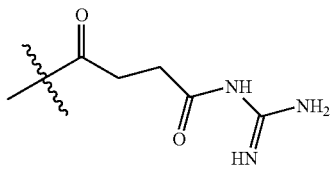 Z53 |
| 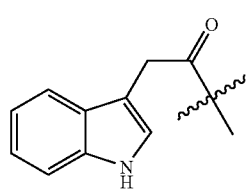 Z47 | 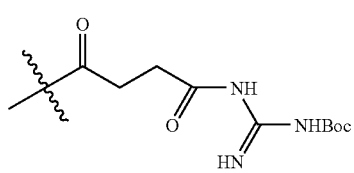 Z55 |
| 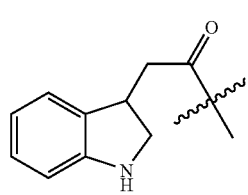 Z48 | Z56 |

-continued

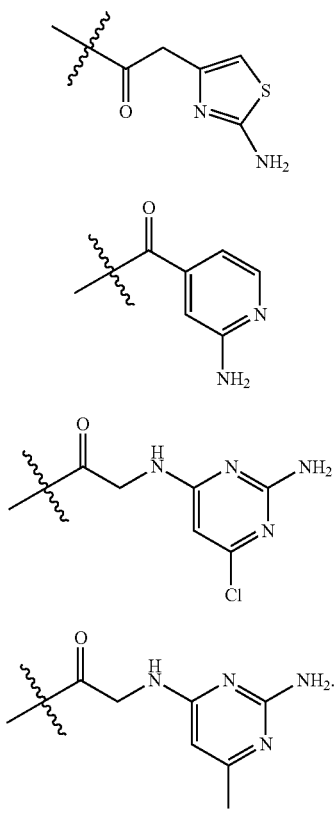

18. A library of compounds containing a plurality of compounds of formula 1 according to claim 1.

19. A compound of formula I

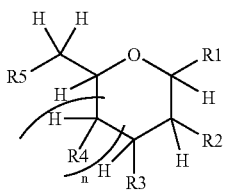

formula I wherein, n is 0 or 1;
R1 is XR wherein,
X is selected from S; S=O and SO$_2$,
R is a moiety selected from the group consisting of: C1 to C9 alkyl, C2 to C15 alkenyl, C2 to C15 alkynyl, C1 to C15 heteroalkyl, C6 to C15 aryl, C6 to C15 heteroaryl, C6 to C15 arylalkyl or C6 to C15 heteroarylalkyl; which moiety R is optionally substituted, cyclic or acyclic, branched and/or linear,
R2 is N(Y)Z,
R3 is OR, where in each occurrence of the moiety OR, R forms an ether bond,
R4 is selected from the group consisting of OH, OR and N(Y)Z,
R5 is selected from the group consisting of OH and OR,
such that when n is 1, one, but not both, of R4 and R5 is OH,
where more than one of R3, R4, and R5 are OR, the OR groups at R3 and R4 or R5 are different, Z is selected from hydrogen or R and Y is selected from the following, where G denotes the point of connection to the nitrogen atom in N(Y)Z,

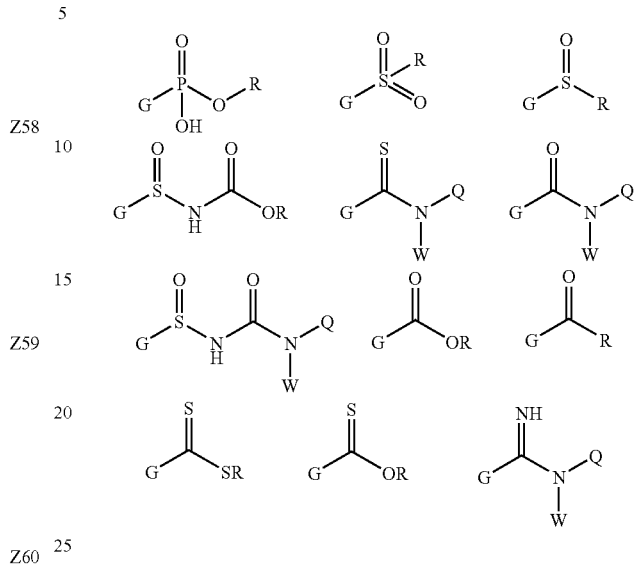

and the groups Q and W are independently selected from hydrogen or R as is defined above, and Q and W may combine to form a cycle,
the groups Z and Y may combine to form a cycle,
the groups R1 to R5 may not combine together to form a cycle,
  with the proviso that where two groups in the compound of formula I are N(Y)Z, these groups are different,
  with the further proviso that N(Y)Z may not be trifluoroacetamido, acetamido,
  with the further proviso that the group R may not be or contain another saccharide moiety; and wherein the optional substituents are selected from the group consisting of OH, NO, NO$_2$, NH$_2$, N$_3$, halogen, CF$_3$, CHF$_2$, CH$_2$F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, aminoaryl, aminoheteroaryl, thioalkyl, thioaryl or thioheteroaryl, which may be further substituted.

20. A compound of formula I

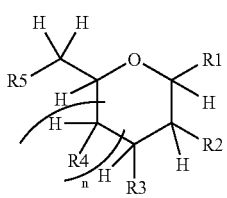

formula I wherein, n is 0 or 1;
R1 is XR wherein,
X is selected from O; S; S=O and SO$_2$,
R is a moiety selected from the group consisting of: C1 to C9 alkyl, C2 to C15 alkenyl, C2 to C15 alkynyl, C1 to C15 heteroalkyl, C6 to C15 aryl, C6 to C15 heteroaryl, C6 to C15 arylalkyl or C6 to C15 heteroarylalkyl; which moiety R is optionally substituted, cyclic or acyclic, branched and/or linear, R2 is N(Y)Z, R3 is OR, where in each occurrence of the moiety OR, R forms an ether bond, R4 is N(Y)Z, R5 is OH, such that when n is 1, one, but not both, of R4 and R5 is OH, where more than one of R3, R4, and R5 are OR, the OR groups at R3 and R4 or R5 are different, Z is selected from hydrogen or R and Y is selected from the following, where G denotes the point of connection to the nitrogen atom in N(Y)Z,

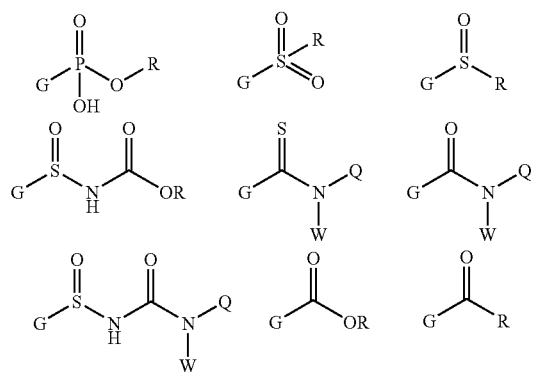

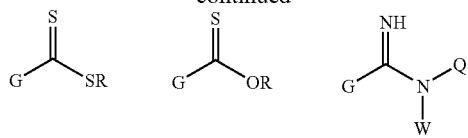

and the groups Q and W are independently selected from hydrogen or R as is defined above, and Q and W may combine to form a cycle, the groups Z and Y may combine to form a cycle, the groups R1 to R5 may not combine together to form a cycle, with the proviso that where two groups in the compound of formula I are N(Y)Z, these groups are different, with the further proviso that N(Y)Z may not be trifluoroacetamido, acetamido, with the further proviso that the group R may not be or contain another saccharide moiety; and wherein the optional substituents are selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, aminoaryl, aminoheteroaryl, thioalkyl, thioaryl or thioheteroaryl, which may be further substituted.

* * * * *